US009272130B2

(12) United States Patent
Sugawara et al.

(10) Patent No.: US 9,272,130 B2
(45) Date of Patent: Mar. 1, 2016

(54) LIVING BODY STIMULATING ELECTRODE, LIVING BODY STIMULATING ELECTRODE APPARATUS, AND METHOD FOR PRODUCING LIVING BODY STIMULATING ELECTRODE

(71) Applicants: Seiko Instruments Inc., Chiba-shi, Chiba (JP); NIHON KOHDEN CORPORATION, Shinjuku-ku, Tokyo (JP)

(72) Inventors: Ryo Sugawara, Chiba (JP); Tomoo Kobayashi, Chiba (JP); Jun Motogi, Tokyo (JP)

(73) Assignee: SEIKO INSTRUMENTS INC., Chiba (JP)

( * ) Notice: Subject to any disclaimer, the term of this patent is extended or adjusted under 35 U.S.C. 154(b) by 0 days.

(21) Appl. No.: 14/529,913

(22) Filed: Oct. 31, 2014

(65) Prior Publication Data
US 2015/0127081 A1 May 7, 2015

(30) Foreign Application Priority Data
Nov. 1, 2013 (JP) ................................. 2013-228392

(51) Int. Cl.
*A61N 1/00* (2006.01)
*A61N 1/04* (2006.01)
(Continued)

(52) U.S. Cl.
CPC ............... *A61N 1/0456* (2013.01); *A61B 5/05* (2013.01); *A61B 5/4005* (2013.01);
(Continued)

(58) Field of Classification Search
CPC . A61N 1/0456; A61N 1/0488; A61N 1/0472; A61N 1/0502; H05K 3/306; A61B 5/04085; A61B 5/0492
See application file for complete search history.

(56) References Cited

U.S. PATENT DOCUMENTS

2001/0031916 A1* 10/2001 Bennett ................ A61B 5/4821
600/383
2013/0274583 A1* 10/2013 Heck .................... A61B 5/0488
600/383

FOREIGN PATENT DOCUMENTS

| EP | 2 174 589 A1 | 4/2010 |
| EP | 2 561 906 A1 | 2/2013 |
| JP | 2010-213929 A | 9/2010 |
| JP | 2013-154023 A | 8/2013 |
| JP | 2013-154024 A | 8/2013 |
| JP | 2013-154025 A | 8/2013 |
| JP | 2013-154026 A | 8/2013 |

(Continued)

OTHER PUBLICATIONS

Extended European Search Report in corresponding European Application No. 14191554.6, dated Mar. 9, 2015, 6 pages.

*Primary Examiner* — Robert N Wieland
(74) *Attorney, Agent, or Firm* — Brinks Gilson & Lione

(57) ABSTRACT

Provided are a living body stimulating electrode, a living body stimulating electrode apparatus, and a method for producing a living body stimulating electrode. The living body stimulating electrode has a flexible circuit board (FPC) between a living body stimulating electrode and a resin part. The resin part and the FPC are fixed with the living body stimulating electrode. Specifically, the flexible circuit board is disposed between the living body stimulating electrode and the resin part, and one or both of a stimulating electrode and a contact electrode constituting the living body stimulating electrode have an engaging part having a pressing part and a fixing part. The pressing part presses the flexible circuit board onto the resin part. Simultaneously, the fixing part is penetrated through a through hole formed in the flexible circuit board and pressed into a hole formed in the resin part, thereby fixed to and held by the resin part. The engaging part may be subjected to a chamfering process (the edge may be chamfered into an angulated plane or a round plane) to form an inclined plane or a curved (round) plane.

10 Claims, 19 Drawing Sheets

(51) Int. Cl.
*A61B 5/05* (2006.01)
*A61B 5/00* (2006.01)
*H05K 3/30* (2006.01)

(52) U.S. Cl.
CPC ........... *A61B 5/4047* (2013.01); *A61N 1/0476* (2013.01); *A61N 1/0488* (2013.01); *H05K 3/306* (2013.01); *Y10T 29/49133* (2015.01)

(56) References Cited

FOREIGN PATENT DOCUMENTS

| | | |
|---|---|---|
| JP | 2014-39878 A | 3/2014 |
| KR | 10-2012-0071978 A | 7/2012 |

* cited by examiner (a)

(b)

Fig. 5A
Fig. 5B
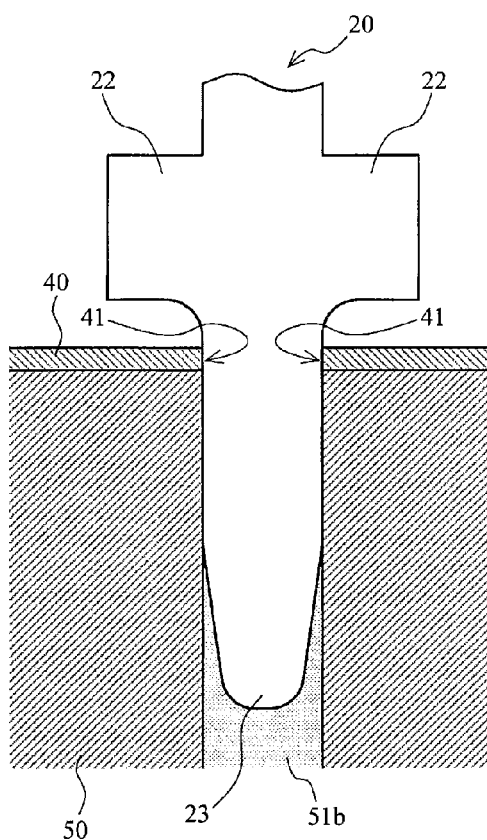
(a)
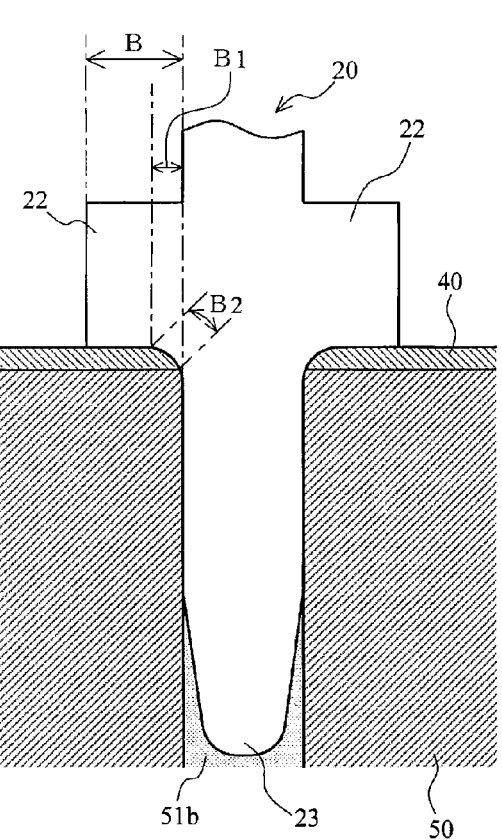
(b)

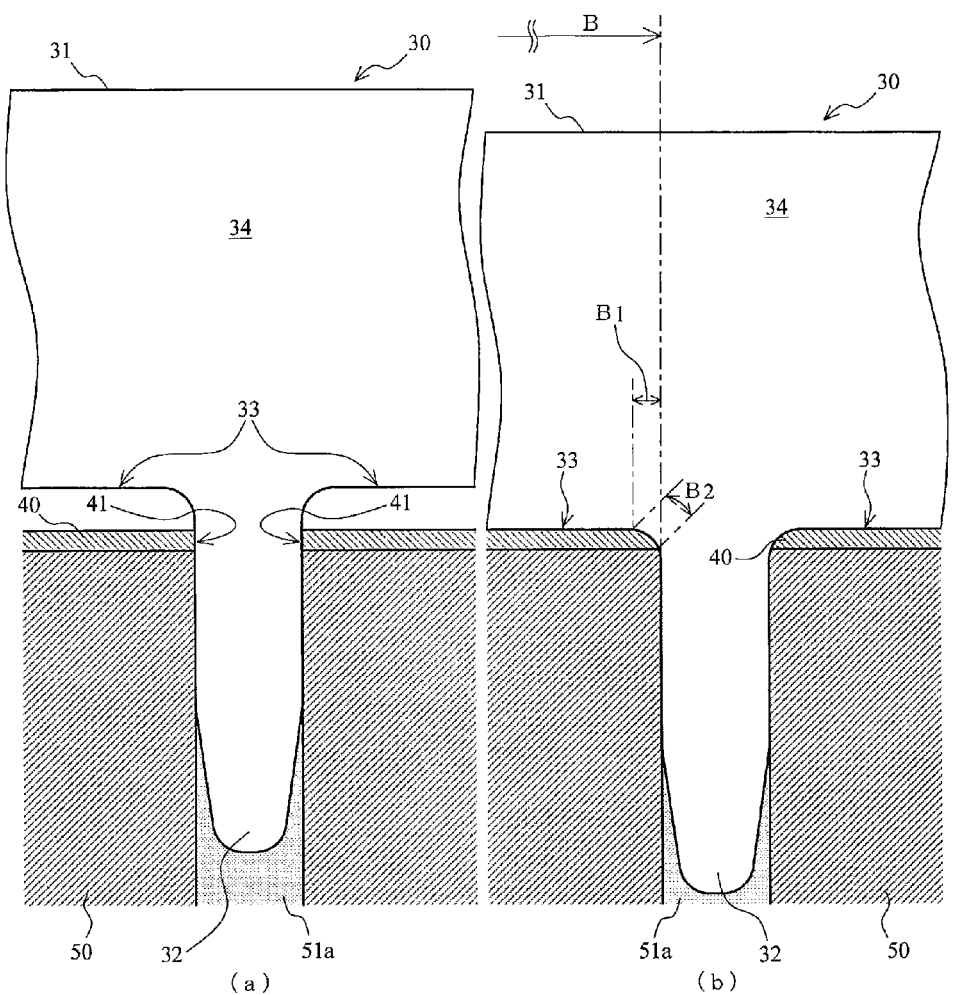

Fig. 7A
Fig. 7B
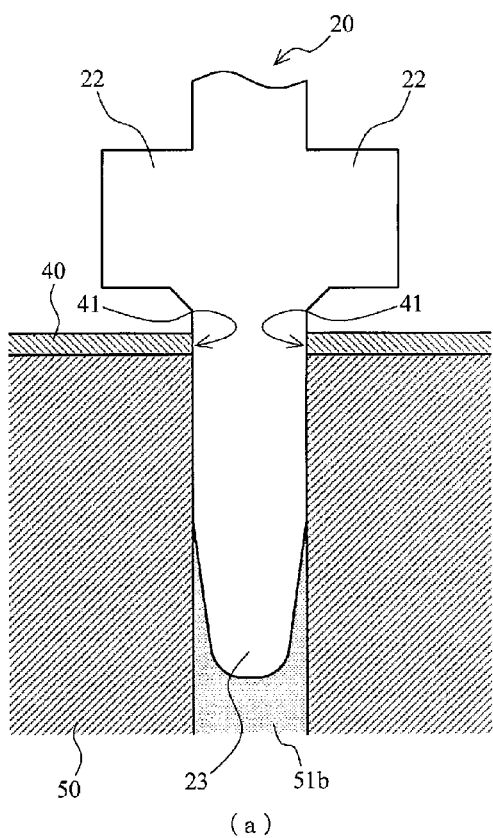
(a)
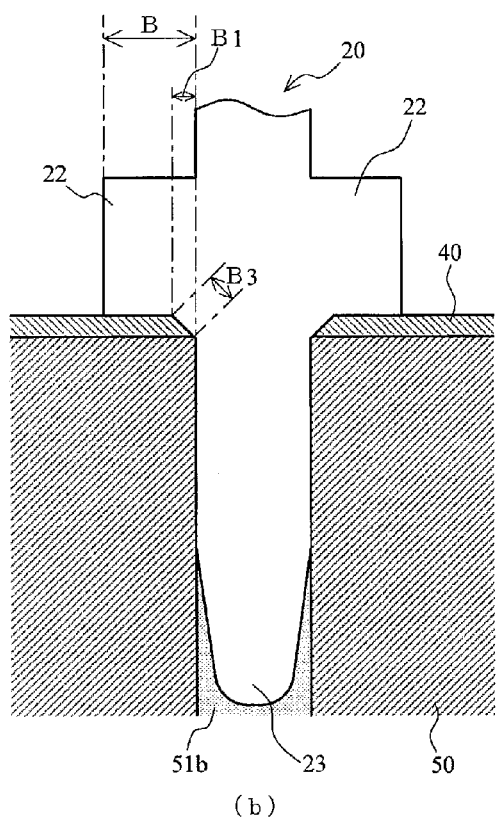
(b)

| Example | Board material | Shape of terminal connecting portion | Dimension (mm) | Terminal withdrawing strength (kgf) | Dispersion of implantation height (mm) | Rate of occurrence of conduction failure (%) |
|---|---|---|---|---|---|---|
| G | PPS | flat | - | 1.0 | 0.01 | 10 |
| A | PPS | R | 0.1 | 1.0 | 0.01 | 0 |
| B | PPS | R | 0.2 | 1.0 | 0.01 | 0 |
| C | PPS | R | 0.3 | 1.0 | 0.01 | 0 |
| D | PPS | C | 0.1 | 1.0 | 0.01 | 0 |
| E | PPS | C | 0.2 | 1.0 | 0.01 | 0 |
| F | PPS | C | 0.3 | 1.0 | 0.01 | 0 |
| H | PP | R | 0.1 | 0.4 | 0.02 | 0 |
| I | PC | R | 0.1 | 0.5 | 0.02 | 0 |

LIVING BODY STIMULATING ELECTRODE, LIVING BODY STIMULATING ELECTRODE APPARATUS, AND METHOD FOR PRODUCING LIVING BODY STIMULATING ELECTRODE

RELATED APPLICATIONS

This application claims priority under 35 U.S.C. §119 to Japanese Patent Application No. 2013-228392 filed on Nov. 1, 2013, the entire content of which is hereby incorporated by reference.

BACKGROUND OF THE INVENTION

1. Field of the Invention

The present invention relates to a living body stimulating electrode, a living body stimulating electrode apparatus, and a method for producing a living body stimulating electrode, and relates, for example, to one that is mounted on the skin and stimulates a pain sensory nerve.

2. Description of the Related Art

For clinical investigations of diabetes and brain waves, such a method has been proposed that a pair of electrodes containing a cathode and an anode is mounted on an end of the finger of the subject or the like, and the pain sense of the subject is stimulated thereby by applying an electric current thereto.

For example, in the case of diabetes where the nerve tissue of the patient is degenerated with the progress of the disease, clues to the condition of the disease of the subject may be found by applying electric stimulation to the pain sensory nerve of the subject and investigating the reaction in the subject.

As the electrode for stimulating a pain sense, the following have been proposed.

JP-A-2010-213929 describes a skin stimulating electrode apparatus that has an insulating part capable of retaining relative positions of a positive electrode and a negative electrode, thereby retaining the difference in height between the tip of the positive electrode and the tip of the negative electrode, which are in contact with the skin.

JP-A-2013-154023, JP-A-2013-154024 and JP-A-2013-154025 each describe a living body stimulating electrode apparatus that has a stimulating electrode having an edge line and stimulating a pain sensory nerve and a contact electrode forming a pair with the stimulating electrode, which are integrated with each other from the portion in contact with the skin to the portion having connectors to wire leads, and are fixed to a resin chassis through insert molding or thermal caulking.

JP-A-2013-154026 describes a living body stimulating electrode apparatus that has a stimulating electrode and a contact electrode, which are each formed solely at the skin contact portions, in which leg parts provided on each of the stimulating electrode and the contact electrode are press fitted into through holes formed in a resin part, thereby fixing the electrodes to the resin part, and simultaneously connecting the electrodes electrically to circuits provided on the inner peripheral surface of the through hole and the back surface of the resin part.

The living body stimulating electrode may have factors of impairing the sense of electric stimulation, for example, due to the weights of the electric parts and the devices itself, the weight of the wire leads (copper wire) for conducting electricity, and the tensile force formed by handling the wire leads for fixing or the like. In addition, there is an increasing demand of a metal terminal (living body stimulating electrode) that is capable of controlling more complex electric signals.

In the aforementioned ordinary electrodes having a wire lead formed of copper wire connected thereto, a complex circuit applied thereto may increase the factors including the weight of the wire lead and the tensile force, which are desirably reduced.

SUMMARY OF THE INVENTION

Under the circumstances, an object of the invention is to provide a living body stimulating electrode, in which the various factors of impairing the sense of electric stimulation are reduced as much as possible without increase of the weight of the wire leads by forming the circuit of the wire lead as an FPC (i.e., a flexible printed circuit, which may also be referred to as a flexible board or a flexible circuit board), thereby providing a mechanism capable of applying pure electric stimulation to a nerve fiber.

Another object of the invention is to ensure the electric connection to the circuit of the flexible circuit board.

Still another object of the invention is to achieve a mechanism capable of controlling complex electric signals.

For achieving the aforementioned objects of the invention, the following embodiments may be provided.

An embodiment 1 of the invention relates to a living body stimulating electrode containing:

a first electrode that has at a tip of one end thereof a stimulating part that has an acute angled shape stimulating a skin of a living body, a second electrode that has at a tip of one end thereof a contact part that is in contact with a skin of a living body through a line or a plane and is formed with a prescribed positional relationship to the stimulating part, an engaging part that is formed at least one of the other end of the first electrode and the other end of the second electrode, the engaging part having a fixing part that extends from the one end toward a direction to the other end, and a pressing part that extends in a side direction, an insulating board that fixes and holds the fixing part, and a flexible circuit board that is disposed between the first electrode and the second electrode, and the insulating board, and has a circuit that is electrically connected to each of the first electrode and the second electrode, the engaging part being fixed to and held by the insulating board by inserting the fixing part into the insulating board with penetration through the flexible circuit board, and thereby the pressing part being in contact with the circuit and pressing and fixing the flexible circuit board to the insulating board.

An embodiment 2 of the invention relates to the living body stimulating electrode according to the embodiment 1, wherein the fixing part and the pressing part are continuous with at least a part thereof through an inclined plane or a curved plane, and a portion of the inclined plane or the curved plane on the side of the fixing part is fixed to and held by the insulating board, whereas the other portion of the inclined plane or the curved plane on the side of the pressing part is in contact with the circuit, and presses and fixes the flexible circuit board to the insulating board.

An embodiment 3 of the invention relates to the living body stimulating electrode according to the embodiment 1 or 2, wherein the flexible circuit board has a first hole having such a diameter that the fixing part of the engaging part is penetrated through the hole, but the pressing part thereof is not penetrated through the hole, and in the first electrode, the second electrode and the flexible circuit board, the fixing part is penetrated through the first hole and is embedded in the insulating board and fixed thereto and held thereby, and thereby the pressing part is in contact with the circuit and presses and fixes the flexible circuit board.

An embodiment 4 of the invention relates to the living body stimulating electrode according to any one of the embodiments 1 to 3, wherein the fixing part has a polygonal cross sectional shape, and the insulating board has a depressed part or a hole fixing and holding the fixing part, and having an opening having a circular shape.

An embodiment 5 of the invention relates to the living body stimulating electrode according to any one of the embodiments 1 to 4, wherein the depressed part or the hole formed in the insulating board and the fixing part are fixed to each other by interference fit.

An embodiment 6 of the invention relates to the living body stimulating electrode according to any one of the embodiments 1 to 5, wherein the insulating board contains a polyphenylene sulfide resin.

An embodiment 7 of the invention relates to the living body stimulating electrode according to any one of the embodiments 1 to 6, wherein the living body stimulating electrode contains plural electrode pairs each containing a combination of the first electrode and the second electrode.

An embodiment 8 of the invention relates to a living body stimulating electrode apparatus containing the living body stimulating electrode according to any one of the embodiments 1 to 7, and a cushioning member that is fixed to the insulating board by sticking to a surface thereof having the first electrode and the second electrode fixed thereto and held thereby, and has through holes, from which the first electrode and the second electrode fixed to and held by the insulating board protrude.

An embodiment 9 of the invention relates to the living body stimulating electrode apparatus according to the embodiment 8, wherein the flexible circuit board has a second hole in at least a part, and the cushioning member and the insulating board are fixed to each other by sticking through the second hole.

An embodiment 10 of the invention relates to a method for producing a living body stimulating electrode containing a first electrode that has at a tip of one end thereof a stimulating part that has an acute angled shape stimulating a skin of a living body, and an engaging part having a fixing part that extends from the one end toward a direction to the other end and a pressing part that extends in a side direction, a second electrode that has at a tip of one end thereof a contact part that is in contact with a skin of a living body through a line or a plane and is formed with a prescribed positional relationship to the stimulating part, and an engaging part having a fixing part that extends from the one end toward a direction to the other end, and a pressing part that extends in a side direction, a flexible circuit board that has a circuit that is electrically connected to each of the first electrode and the second electrode, and an insulating board that has a hole for the fixing part corresponding to the first electrode and a hole for the fixing part corresponding to the second electrode, the method containing a first step of placing the flexible circuit board on the insulating board, a second step of pressing the fixing part of the first electrode into the corresponding hole for the fixing part of the insulating board with penetration through the flexible circuit board, until the pressing part of the first electrode is in electrical contact with the circuit of the flexible circuit board, and at the contact part, the flexible circuit board is pressed and fixed to the insulating board, and a third step of pressing the fixing part of the second electrode into the corresponding hole for the fixing part of the insulating board with penetration through the flexible circuit board, until the pressing part of the second electrode is in electrical contact with the circuit of the flexible circuit board, and at the contact part, the flexible circuit board is pressed and fixed to the insulating board.

According to the embodiments of the invention, the circuit for the wire leads is formed as an FPC, and thereby the various factors of impairing the sense of electric stimulation are reduced as much as possible without increase of the weight of the wire leads, so as to apply pure electric stimulation to a nerve fiber.

According to the embodiments of the invention, furthermore, the electric connection to the circuit of the flexible circuit board is ensured.

According to the embodiments of the invention, furthermore, a mechanism capable of controlling complex electric signals is achieved.

BRIEF DESCRIPTION OF THE DRAWINGS

FIGS. 5A and 5B are schematic enlarged cross sectional views showing an example of an electrode.

FIGS. 6A and 6B are schematic enlarged cross sectional views showing an example of an electrode.

FIGS. 7A and 7B are schematic enlarged cross sectional views showing an example of an electrode.

FIG. 11 is a table showing experimental results.

DETAILED DESCRIPTION OF THE PREFERRED EMBODIMENTS

(1) Summary of the Embodiments

In one embodiment of the invention, the living body stimulating electrode has a flexible circuit board (FPC) between a living body stimulating electrode (i.e., a metal terminal or an electrode terminal) and a resin part (i.e., an insulating board).

In the living body stimulating electrode in the embodiment, the resin part and the FPC are fixed to each other by utilizing the living body stimulating electrode, thereby achieving simultaneously the mechanical and physical connection between the resin part and the flexible circuit board and the electric connection between the flexible circuit board and the living body stimulating electrode.

Specifically, the flexible circuit board is disposed between the living body stimulating electrode and the resin part, and both or one of a stimulating electrode and a contact electrode constituting the living body stimulating electrode has an engaging part having a pressing part and a fixing part.

The pressing part presses and fixes the flexible circuit board to the resin part. Simultaneously, the fixing part is penetrated through a through hole formed in the flexible circuit board and pressed into a hole formed in the resin part, and thereby the flexible circuit board is fixed to and held by the resin part.

According to the structure, the flexible circuit board is physically fixed to the resin part, and simultaneously the electrodes are electrically connected to the circuit of the flexible circuit board.

Furthermore, the engaging part is chamfered to form an inclined plane or a curved (round) plane (i.e., the edge is chamfered into an angulated plane or a round plane).

According to the structure, the electric connection is enhanced in reliability.

(2) Details of Embodiments

Preferred embodiments will be described in detail with reference to FIGS. 1 to 19.

In all the embodiments and modified embodiments, the term "hole" includes all a through hole, a depressed part formed on a plane, and a non-through hole.

First Embodiment

A living body stimulating electrode 1 according to a first embodiment will be described.

Figure 1:
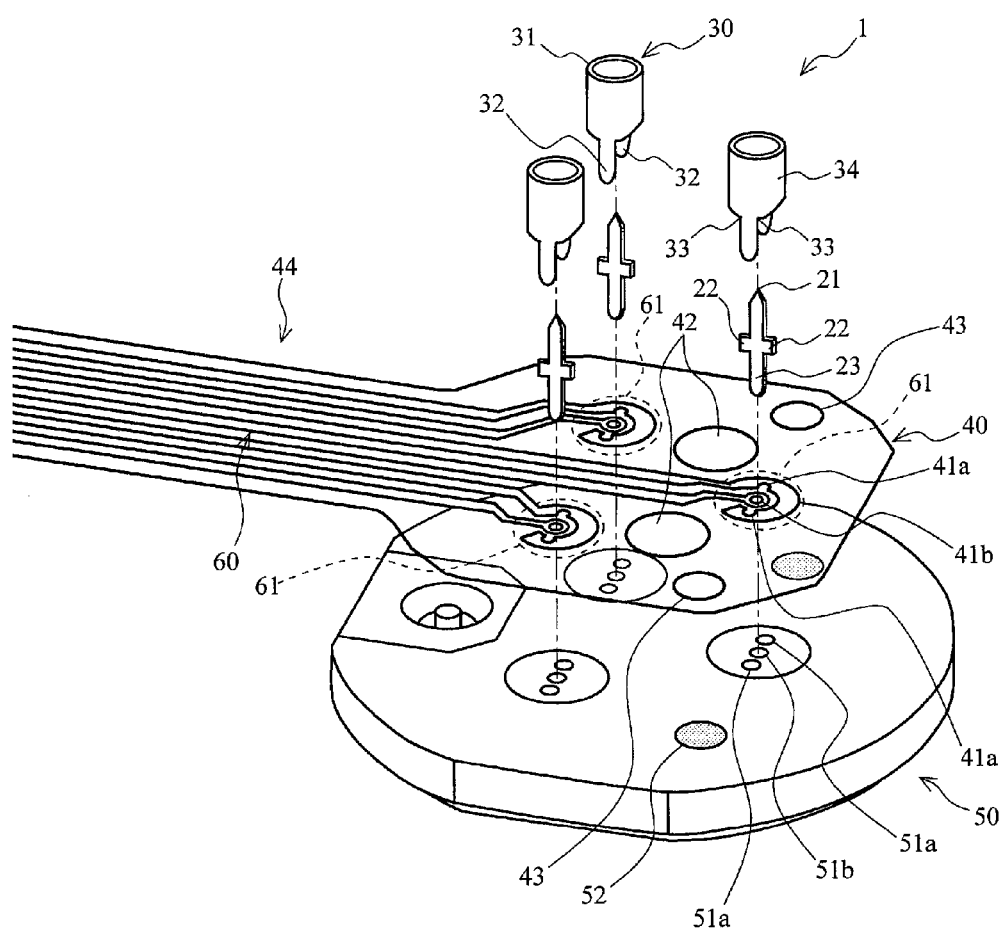
FIG. 1 is a perspective view showing an example of a living body stimulating electrode.

FIG. 1 is a perspective view showing the living body stimulating electrode 1 according to the first embodiment, and is an illustration showing the state before fixing (fixing and holding) the devices (constitutional parts) to a resin board (a resin part 50) as a fixing board.

Figure 2:
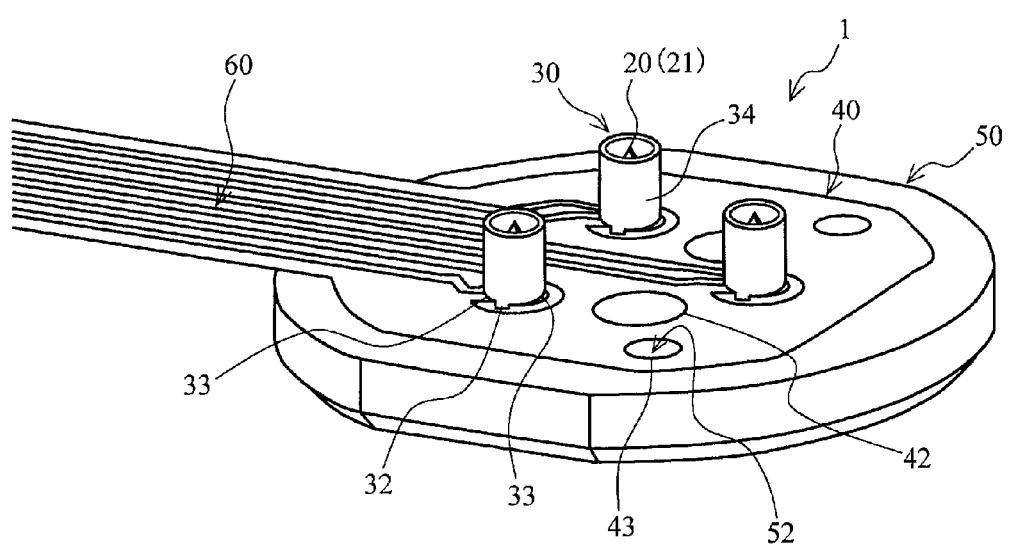
FIG. 2 is a perspective view showing an example of a living body stimulating electrode.

FIG. 2 is a perspective view showing the living body stimulating electrode 1 according to the first embodiment, and is an illustration showing the state where the devices (constitutional parts) shown in FIG. 1 are fixed to (fixed to and held by) the resin board (the resin part 50) as a fixing board. In FIG. 2, a contact electrode fixing part 32 and a contact electrode pressing part 33 are shown to depict the positional relationship thereof, but in the actual implementation, the contact electrode fixing part 32 is entirely embedded in the resin part 50.

The living body stimulating electrode 1 according to the first embodiment is constituted by a stimulating electrode 20, a contact electrode 30, a flexible circuit board 40, the resin part 50, and the like.

The flexible circuit board 40 is a flexible printed circuit (FPC) obtained by laminating an insulating thin flexible base film as a substrate and an electric circuit (wiring) formed of a conductive metal, such as a copper foil.

In the first embodiment, the flexible circuit board 40 is used instead of a wire lead formed of copper wire having been ordinarily used, and is disposed between the pairs of electrodes (including the stimulating electrode 20 and the contact electrode 30) and the resin part 50 (which are described in detail later).

The flexible circuit board 40 used in the first embodiment, for example, has a thickness of 0.08 mm and has a fixing part hole F 41, a stick fixing hole 42, a positioning hole F 43 and a lead part 44.

In this embodiment, the fixing part hole F 41 formed in the flexible circuit board 40 is a through hole, through which the fixing part (i.e., the stimulating electrode fixing part 23 or the contact electrode fixing part 32) of the metal terminal (the electrode terminal, i.e., the stimulating electrode 20 or the contact electrode 30) is penetrated.

In the following, the fixing part hole F 41 is referred to for the penetration of the fixing part of one or both of the electrode terminals, whereas a fixing part hole F 41a is referred to for the penetration of the contact electrode fixing part 32 of the contact electrode 30, and a fixing part hole F 41b is referred to for the penetration of the stimulating electrode fixing part 23 of the stimulating electrode 20.

The contact electrode fixing part 32 of the contact electrode 30 (described later) is inserted in and penetrated through the fixing part hole F 41a, and the stimulating electrode fixing part 23 of the stimulating electrode 20 is inserted in and penetrated through the fixing part hole F 41b.

In the first embodiment, as shown in FIGS. 1 and 2, the fixing part hole F 41 as a contact pattern hole of the flexible circuit board 40 has a circular opening, and the fixing part (i.e., the stimulating electrode fixing part 23 or the contact electrode fixing part 32) of the terminal (i.e., the stimulating electrode 20 or the contact electrode 30) to be inserted into the opening has a polygonal cross sectional shape, but the fixing part holes F 41a and 41b may not necessarily have a circular shape.

The stick fixing hole 42 formed on the flexible circuit board 40 is a hole for fixing by sticking a cushioning member 70 (see FIGS. 9A and 9B) described later and the resin part 50.

The positioning hole F 43 formed on the flexible circuit board 40 is a hole that is utilized for positioning in the assembling process described later.

The lead part 44 is a conductor wire part for connecting the circuit 60 formed on the flexible circuit board 40 to a connector 45 (see FIGS. 9A, 9B, and 10) supplying an electric current to the circuit 60.

The connector 45 has no problem in weight increase since the connector 45 is not provided on the side of the electrode terminals, i.e., the side that is in contact with the living body for measuring electric stimulation.

The circuit 60 is formed by laminating a metal foil, such as a copper foil, and etching the metal layer formed therewith.

A connecting part 61 is an area of the circuit for electrically connecting the circuit 60 and the electrode terminal (i.e., the stimulating electrode 20 or the contacting electrode 30), and circuits are formed around the fixing part hole F 41a for connecting to the contact electrode 30 and around the fixing part hole F 41b for connecting to the stimulating electrode 20. In the connecting part 61, the circuits are formed within a range that the pressing part of the electrode terminal (i.e., the stimulating electrode pressing part 22 or the contact electrode pressing part 33) reaches.

One or plural connecting parts 61 may be formed on the flexible circuit board 40 depending on the objects and purposes.

In this embodiment, three electrode pairs each of which is formed of one stimulating electrode 20 and one contact electrode 30 are provided, to each of which a circuit is independently connected. According to the structure, control of complex electric signals may be enabled.

In this embodiment, the engaging part (i.e., the stimulating electrode pressing part 22 and the stimulating electrode fixing part 23 or the contact electrode fixing part 32 and the contact electrode pressing part 33) presses and fixes the flexible circuit board 40 to the resin part 50. According to the structure, the flexible circuit board 40 may be effectively prevented from being floated at the center part thereof from the resin part 50.

In the first embodiment as shown above, the use of the flexible circuit board 40 achieves a complex circuit without the use of many wire leads using copper wire, thereby providing the living body stimulating electrode 1 having a light weight capable of controlling complex electric stimulation.

The resin part 50 is a fixing member that functions as an insulating board and has a flat surface. The resin part 50 has a fixing part hole J 51 for fixing the electrode pair formed of the stimulating electrode 20 and the contact electrode 30 and a positioning hole J 52 used in the assembling process described later.

In the following, the fixing part hole J 51 is referred to for fixing the fixing part of one or both of the electrode terminals, whereas a fixing part hole J 51a is referred to for fixing the contact electrode fixing part 32 of the contact electrode 30, and a fixing part hole J 51b is referred to for fixing the stimulating electrode fixing part 23 of the stimulating electrode 20.

The resin part 50 has three groups of holes (i.e., a pair of the fixing part hole J 51a and the fixing part hole J 51b) at the three vertices of the equilateral triangle having the center of gravity at the center of the resin part 50.

In the resin part 50, one electrode pair is disposed in one group of holes to form one living body stimulating electrode, and the electrode pairs are disposed in the three vertices of the equilateral triangle to form three living body stimulating electrodes. The resin part 50 thus may be used as both a resin part for one electrode and a resin part for three electrodes.

The resin part 50 is formed of a resin having an approximately cylindrical shape and has, for example, a diameter of approximately from 10 to 16 mm and a thickness of approximately from 2 to 4 mm.

As shown in FIG. 2, the electrode pair, which is the pair of the stimulating electrode 20 and the contact electrode 30, is disposed on the surface of the resin part 50 and thus protrudes from the center parts of the resin part 50. The protruding amount of a cylindrical part 34 of the contact electrode 30 may be, for example, approximately 1 mm.

The fixing part hole J 51 formed in the resin part 50 is for fixing and holding the stimulating electrode 20 or the contact electrode 30 described later. More specifically, the contact electrode fixing part 32 of the contact electrode 30 is pressed into the fixing part hole J 51a, and the contact electrode fixing part 32 is engaged with the fixing part hole J 51a, whereas the stimulating electrode fixing part 23 of the stimulating electrode 20 is pressed into the fixing part hole J 51b, and the stimulating electrode fixing part 23 is engaged with the fixing part hole J 51b.

Accordingly, while the details are described later, the stimulating electrode 20 is fixed to and held by the resin part 50 by embedding the stimulating electrode fixing part 23 in the resin part 50. Similarly, the contact electrode 30 is fixed to and held by the resin part 50 by embedding the contact electrode fixing part 32 in the resin part 50.

In the first embodiment, as shown in FIG. 2, the electrode pairs are disposed along the circumference of the concentric circle with the bottom surface of the resin part 50. Accordingly, on pressing the living body stimulating electrode 1 onto the skin, the force applied thereto may be distributed to the electrode pairs in a well-balanced manner.

The resin part 50 may be formed of any resin that is harmless to the living body and has insulating property, and examples thereof used include a polypropylene resin (PP) and a polycarbonate resin (PC). The resin part 50 may be formed of ceramics.

The metal terminal (electrode) according to the first embodiment will be described.

As shown in FIG. 1, the stimulating electrode 20 according to the first embodiment is an electrode for stimulating a pain sensory nerve that has the stimulating part 21 at the tip thereof, the stimulating electrode pressing part 22 protruding in the side direction, and the stimulating electrode fixing part 23 provided at the opposite tip to the stimulating part 21.

The stimulating electrode 20 may be formed by punching a metal plate that is harmless to the living body, such as SUS304 and SUS316. Other metals that are harmless to the living body may be used, and a material plated with a metal that is harmless to the living body, such as gold, may also be used.

The stimulating part 21 has an acute angled shape with a minute area and is stuck in the skin of the living body by pressing. In the first embodiment, for example, the stimulating electrode 21 has a height in the axial direction (longitudinal direction) of 2 mm, a width in the side direction (shorter direction) of 1 mm and a diameter of 1.5 mm.

The stimulating electrode 20 has, in addition to the stimulating part 21, an engaging part that achieves fixation to the resin part 50, and the engaging part is constituted by the stimulating electrode pressing part 22 and the stimulating electrode fixing part 23.

Figure 3A:
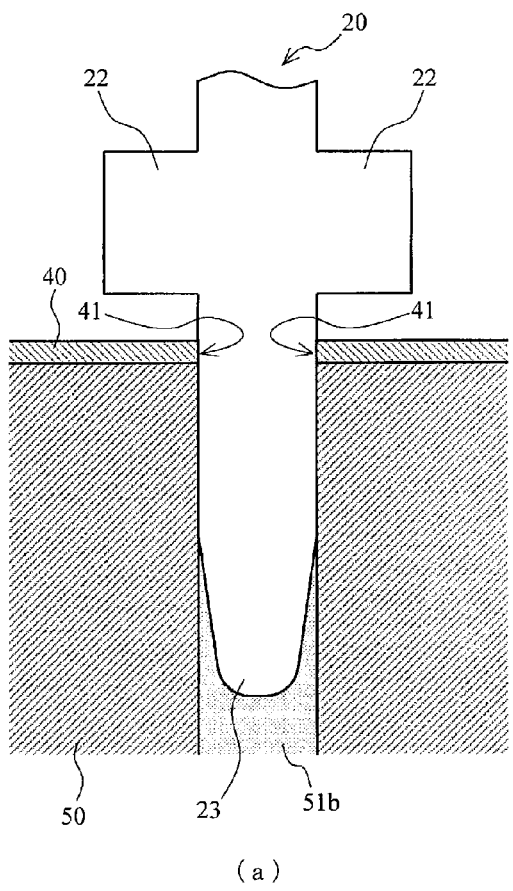
FIGS. 3A and 3B are schematic enlarged cross sectional views showing an example of a fixed state (electric connection) of an electrode.
Figure 3B:
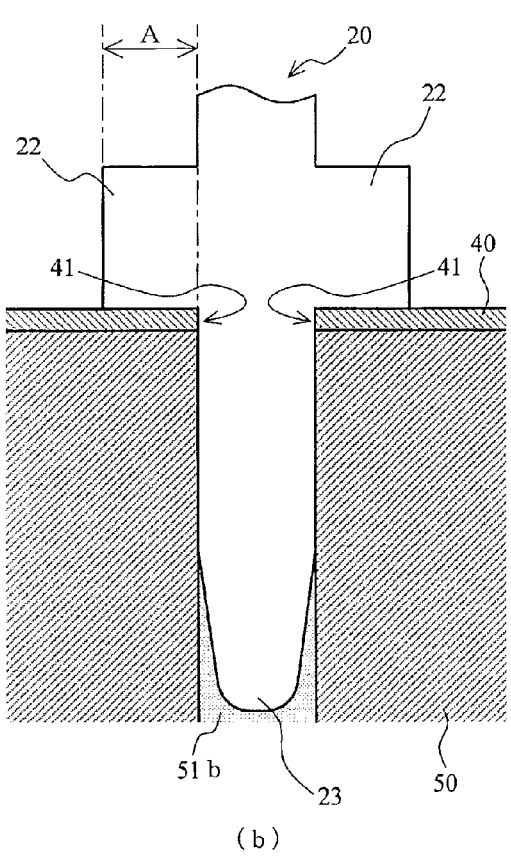

FIGS. 3A and 3B are enlarged cross sectional views showing the fixing state (electrically connecting state) of the stimulating electrode 20 to the resin part 50 in the first embodiment.

FIG. 3A shows the state in the course of the fixation of the stimulating electrode 20 to the resin part 50 with the flexible circuit board 40 intervening between them, and FIG. 3B shows the state where the connection (fixation) is completed.

In the first embodiment, the stimulating electrode pressing part 22 functioning as a part of the engaging part of the stimulating electrode 20 protrudes in the width direction (shorter direction) in the side direction of the approximate center in the longitudinal direction of the stimulating electrode 20.

The stimulating electrode pressing part 22 thus formed has the function of a stopper that restricts the insertion amount on pressing the stimulating electrode fixing part 23 of the stimulating electrode 20 into the hole of the resin part 50 (i.e., the fixing part hole J 51b), and also has the function of electrically connecting the stimulating electrode 20 to the circuit of the flexible circuit board 40 present in the vicinity of the opening of the hole of the resin part 50 (i.e., the fixing part hole J 51b), the function of fixing the flexible circuit board 40 to the resin part 50 by pressing, and the function of mechanically connecting the stimulating electrode 20 to the resin part 50. The overlap for electric connection A for the electric connection of the electrode and the circuit is shown in FIG. 3B.

The stimulating electrode pressing part 22 functions as a stopper, and therefore the distance between the end surface of the stimulating electrode pressing part 22 on the side of the stimulating part 21 (i.e., the surface thereof opposite to the surface facing the resin part 50) and the stimulating part 21 of the stimulating electrode 22 is a prescribed value.

In the first embodiment, the stimulating electrode pressing part 22 is formed on both sides, but may be formed on only one side.

In the case where the stimulating electrode pressing part 22 is formed on both sides as in the first embodiment, the positions of the end surfaces of the stimulating electrode pressing parts 22 on the side of the stimulating part 21 are at the same position (i.e., the distances thereof from the stimulating part 21 are the prescribed value).

The stimulating electrode fixing part 23, which functions as a part of the engaging part of the stimulating electrode 20, is a single leg-like member that is provided in the stimulating electrode 20 on the opposite side in the longitudinal direction to the stimulating part 21. The stimulating electrode fixing part 23 has such a function that the stimulating electrode 20 is fixed to the resin part 50 with the flexible circuit board 40 intervening between them, and simultaneously the stimulating electrode 20 is electrically connected to the circuit of the flexible circuit board 40 disposed on one surface of the resin part 50.

Figures 4A, 4B:
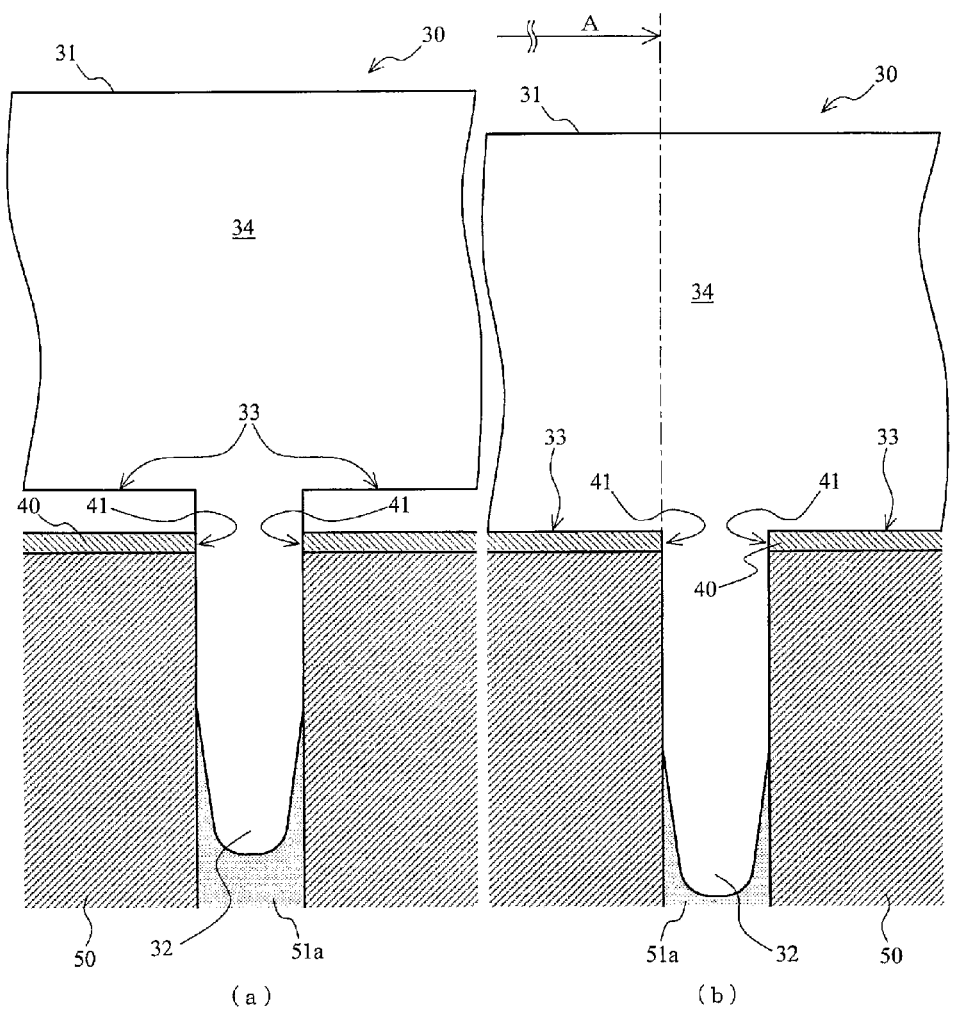
FIGS. 4A and 4B are schematic enlarged cross sectional views showing an example of an electrode.

While the stimulating electrode pressing part 22 functioning as a part of the engaging part of the stimulating electrode 20 is described in FIGS. 3A and 3B as an example, the fixation (electric connection) of the contact electrode 30 to the resin part 50 may have the similar embodiment as shown in FIGS. 4A and 4B.

Returning to FIGS. 1 and 2, the contact electrode 30 has a contact part 31, a contact electrode fixing part 32, a contact electrode pressing part 33 and a cylindrical part 34.

The contact electrode 30 may be formed by punching a metal plate formed of the same material as the stimulating electrode 20. More specifically, a rectangular part for forming the cylindrical part 34 and two contact electrode fixing parts 32 are prepared. The rectangular part thus punched is rolled up to make the width direction of the rectangular part directed to the axial direction of the cylindrical part 34, thereby making the cylindrical part 34. The end surface of the cylindrical part 34 on the side having the contact electrode fixing part 32 functions as the contact electrode pressing part 33, and the end surface thereof on the opposite side functions as the contact part 31. In the first embodiment, the contact part 31, which is in contact with the skin, of the contact electrode 30 has a cylindrical shape, but the shape thereof may not necessarily be a cylindrical shape and may be various shapes including a rectangular shape, a triangular shape and a U-shape in cross section.

The end surface of the cylindrical part 34 where the contact electrode fixing part 32 is not formed has the contact part 31, which has a flat shape to be pressed on and in contact with the skin of the living body. The contact part 31 may be in the form of a line or a plane for achieving a function of restricting the sticking depth of the stimulating part 21 of the stimulating electrode 20.

The contact electrode 30 has on the opposite side to the contact part 31 the engaging part achieving fixation to the resin part 50, and the engaging part is constituted by the contact electrode fixing part 32 and the contact electrode pressing part 33.

The contact electrode fixing part 32 functioning as a part of the engaging part of the contact electrode 30 is two leg-like members that each extend from the end surface of the cylindrical part 34 on the opposite side to the contact part 31 in the longitudinal direction of the cylindrical part 34. The contact electrode fixing part 32 has such a function that the contact electrode 30 is fixed to the resin part 50, and simultaneously the contact electrode 30 is electrically connected to the circuit of the flexible circuit board 40 disposed on one surface of the resin part 50.

The two members of the contact electrode fixing part 32 are disposed along the virtual line passing through the center line of the cylindrical part 34. The number of the members constituting the contact electrode fixing part 32 may be only one or three or more.

In the first embodiment as shown in FIGS. 1 and 2, the center line of the stimulating part 21 of the stimulating electrode 20 agrees with the center line of the cylindrical part 34 of the contact electrode 30, and the stimulating part 21 protrudes from the contact part 31 of the contact electrode 30 by approximately from 0 to 0.5 mm.

An electrode pair is constituted by the stimulating electrode 20 and the contact electrode 30 thus disposed, and on pressing the electrode pair to the skin of the living body, the stimulating part 21 is stuck in the skin, and the contact part 31 is in contact with the skin to achieve electric contact with the skin and simultaneously restricts the sticking depth of the stimulating part 21 into the skin.

In the following description, the surface having the electrode pair (i.e., the stimulating electrode 20 and the contact electrode 30) formed thereon is referred to as a front surface, and the opposite surface thereto is referred to as a back surface.

The first embodiment may have, for example, a structure that applies a pulse voltage with the stimulating electrode 20 (i.e., the stimulating part 21) as a cathode and the contact electrode 30 (i.e., the contact part 31) as an anode, but the embodiment is not limited to the structure. Specifically, the stimulating electrode 20 (i.e., the stimulating part 21) may be used as an anode, whereas the contact electrode 30 (i.e., the contact part 31) may be used as a cathode, and the stimulating electrode 20 (i.e., the stimulating part 21) and the contact electrode 30 (i.e., the contact part 31) may be applied with an alternating current voltage or a direct current voltage.

In this embodiment, the stimulating part 21 is stuck in the skin, but the stimulating part 21 may not be necessarily stuck in the skin, but may only dent in the skin depending on the use purpose of the electrode pair.

In the first embodiment, the number of the electrode pairs is three pairs but may be other number of pairs, for example, only one pair or two or four pairs. In the case where plural electrode pairs are formed, even if one (stimulating part 21) of them is stuck in a portion having a low nerve fiber density, it is expected that another electrode pair (stimulating part 21) may be stuck in a portion having a high nerve fiber density. Accordingly, the pain sense may be more definitely stimulated, thereby enhancing the reliability.

In the resin part 50, the holding strength of the metal terminals (i.e., the stimulating electrode 20 and the contact electrode 30), which is the withdrawing strength of the metal terminals, may be determined by the mechanical strength of the resin (i.e., the insulating material) used as the board.

In the first embodiment, accordingly, a polyphenylene sulfide resin (PPS) is used as the resin part 50, and thereby the mechanical connection is enhanced in reliability as shown by the experimental results shown later.

In the case where a ceramic board or the like is used as the resin part 50 instead of the resin board, holes (e.g., depressed parts or through holes) are provided in the ceramic board, and the fixing parts provided in the stimulating electrode 20 and the contact electrode 30 (i.e., the stimulating electrode fixing part 23 and the contact electrode fixing part 32) are pressed into the holes.

In the first embodiment, furthermore, the diagonal dimension in the horizontal cross section of the terminal (i.e., the stimulating electrode 20 or the contact electrode 30), which is to be inserted into the opening of the fixing part hole J 51 (connecting pattern hole) of the resin part 50, is larger than the diameter of the opening of the fixing part hole J 51, thereby fixing them by interference fit.

Instead of the interference fit, the terminal may be fixed by such a fixing method that uses clearance fit and an adhesive. In this case, the diagonal dimension in the cross section of a parallel portion of the terminal (i.e., the stimulating electrode 20 or the contact electrode 30), which is to be inserted into the opening of the fixing part hole J 51 of the resin part 50, is smaller than the diameter of the opening of the fixing part hole J 51.

In the first embodiment as described above, the flexible circuit board 40 is disposed on one surface (i.e., the front surface) of the resin part 50, and the fixing parts provided in the electrode terminals (i.e., the stimulating electrode 20 and the contact electrode 30) are inserted (pressed) in the fixing part holes J 51 formed in the resin part 50, whereby the electrode terminals (i.e., the stimulating electrode 20 and the contact electrode 30), the flexible circuit board 40 and the resin part 50 are fixed to each other, and simultaneously the electrode terminals (i.e., the stimulating electrode 20 and the contact electrode 30) are electrically connected to the circuits of the flexible circuit board 40 in the vicinity of the opening of the fixing part holes J 51.

The stimulating electrode 20 and the contact electrode 30 may be formed from a metal plate by sheet metal processing (press processing including punching process, bending process and drawing process), and thus may be easily mass-produced with high dimensional accuracy.

In the first embodiment as described above, while the flexible circuit board 40 is inserted between the metal terminals (i.e., the first electrode and the second electrode) and the insulating board, the pressing part (i.e., the stimulating electrode pressing part 22 or the contact electrode pressing part 33), which functions as a part of the engaging part of the metal terminal (electrode), presses the contact surface with the flexible circuit board 40, and simultaneously the fixing part (i.e., the stimulating electrode fixing part 23 or the contact electrode fixing part 32) fixes the metal terminal to the insulating board (i.e., the resin part 50). Accordingly, the metal terminal is disposed on (inserted and pressed in) the insulating board just like a terminal embedded in the insulating board, and the flexible circuit board 40 is in a state where it is pressed (fixed) with the metal terminals as pins.

Modified embodiments of the engaging part (i.e., the pressing part and the fixing part) in the first embodiment will be described.

Modified Embodiment 1

FIGS. 5A and 5B are schematic enlarged views describing a stimulating electrode 20 according to a modified embodiment 1 of the first embodiment.

As shown in FIGS. 5A and 5B, the stimulating electrode 20 according to the modified embodiment 1 has an engaging part, which has functions of both a stimulating electrode pressing part 22 in contact with the flexible circuit board 40 and a stimulating electrode fixing part 23 fixed to and held by the resin part 50, and an overlap for electric connection B, in which the stimulating electrode pressing part 22 and the stimulating electrode fixing part 23 are continuous with a curved plane (i.e., a round shape).

Specifically, the engaging part of the stimulating electrode 20 is chamfered to form a round shape (i.e., an overlap for electric connection B2) in a part of the contact surface.

According to the structure of the modified embodiment 1, the overlap for electric connection may be increased by such a length that is obtained by subtracting the overlap for electric connection B1 from the overlap for electric connection B2 (B2>B1) shown in FIGS. 5A and 5B, as compared to the case where the electrode and the circuit are in contact with each other through a flat plane (i.e., the overlap for electric connection A) as shown in FIGS. 3A and 3B.

Furthermore, it is expected by the structure that the local contact strength (i.e., the physical contact strength) may also be increased.

In the case shown in FIGS. 3A and 3B where the electrode and the circuit are in contact with each other through a flat plane, there may be a possibility that the shortage of the insertion depth (embedding depth) of the electrode terminal (i.e., the stimulating electrode 20) causes contact failure. In the structure of the modified embodiment 1, however, the contact part may be enhanced in such an amount that is enhanced by the round shape (i.e., the length obtained by subtracting the overlap for electric connection B1 from the overlap for electric connection B2), thereby further ensuring the contact.

Consequently, the electric connection may be further enhanced in reliability.

Modified Embodiment 2

While the stimulating electrode pressing part 22 functioning as a part of the engaging part of the stimulating electrode 20 is described in FIGS. 5A and 5B as an example, the fixation (electric connection) of the contact electrode 30 to the resin part 50 may have the similar embodiment as shown in FIGS. 6A and 6B.

Modified Embodiment 3

FIGS. 7A and 7B are schematic enlarged views describing an electrode according to a modified embodiment 3 of the embodiment.

While a stimulating electrode 20 is described as an example of the electrode terminal in the modified embodiment 3, the similar structure may be applied to a contact electrode 30.

As shown in FIGS. 7A and 7B, the stimulating electrode 20 according to the modified embodiment 3 has an engaging part, which has functions of both a stimulating electrode pressing part 22 in contact with the flexible circuit board 40 and a stimulating electrode fixing part 23 fixed to and held by the resin part 50, and a portion, in which the stimulating electrode pressing part 22 and the stimulating electrode fixing part 23 are continuous with an inclined plane.

Specifically, the engaging part of the stimulating electrode 20 is chamfered to form a chamfered shape, and an overlap for electric connection B3 is formed in a part of the contact surface.

According to the structure of the modified embodiment 3, the overlap for electric connection may be increased by such a length that is obtained by subtracting the overlap for electric connection B1 from the overlap for electric connection B3 (B3>B1) shown in FIGS. 7A and 7B, as compared to the case where the electrode and the circuit are in contact with each other through a flat plane (i.e., the overlap for electric connection A) as shown in FIGS. 3A and 3B.

Furthermore, it is expected by the structure that the local contact strength (i.e., the physical contact strength) may also be increased.

In the case shown in FIGS. 3A and 3B where the electrode and the circuit are in contact with each other through a flat plane, there may be a possibility that the shortage of the insertion depth (embedding depth) of the stimulating electrode 20 (i.e., the contact electrode 30) causes contact failure. In the structure of the modified embodiment 3, however, the contact part may be enhanced in such an amount that is enhanced by the chamfered shape (i.e., the length obtained by subtracting the overlap for electric connection B1 from the overlap for electric connection B3), thereby further ensuring the contact.

Consequently, the electric connection may be further enhanced in reliability.

Modified Embodiment 4

Figure 8A:
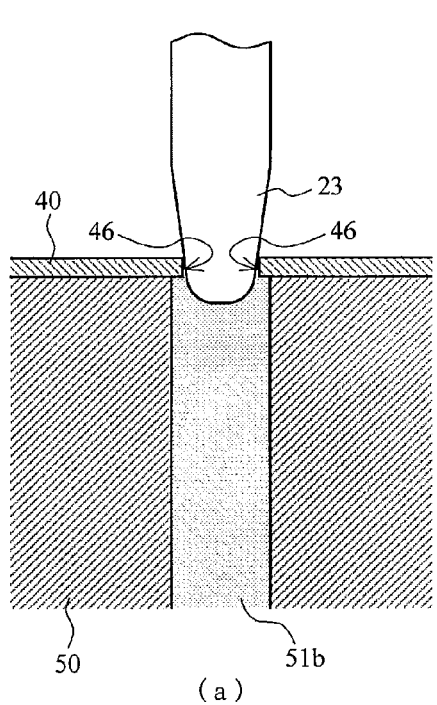
FIGS. 8A, 8B and 8C are schematic enlarged cross sectional views showing an example of an electrode.
Figure 8B:
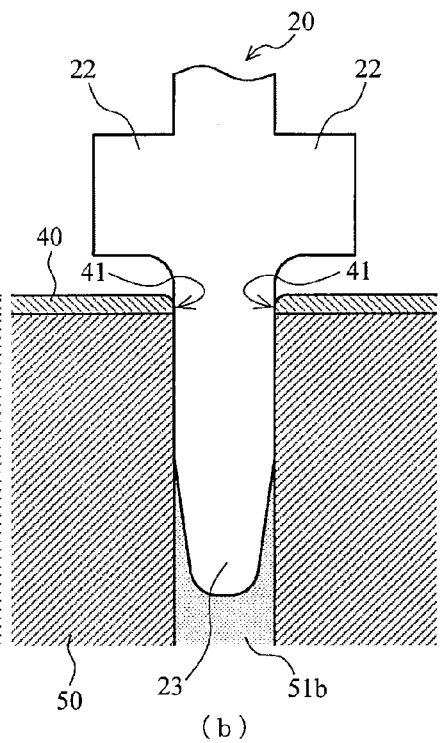
Figure 8C:
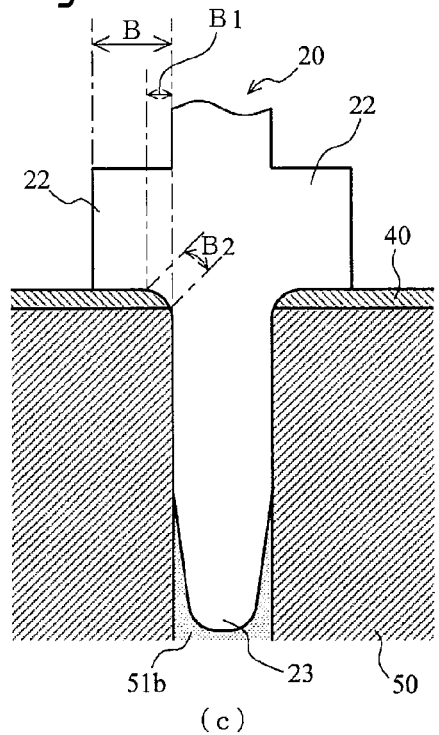

FIGS. 8A, 8B and 8C are schematic enlarged views describing an electrode according to a modified embodiment 4 of the embodiment.

While a stimulating electrode 20 is described as an example of the electrode terminal in the modified embodiment 4, the similar structure may be applied to a contact electrode 30.

As shown in FIG. 8A, in the modified embodiment 4, the flexible circuit board 40 has a fixing part hole F 46 having an opening that is smaller than the opening of the fixing part hole J 51.

As shown in the modified embodiment 4, the fixing part hole F formed in the flexible circuit board 40 for holding the fixing part of the stimulating electrode 20 (or the contact electrode 30) may not necessarily have the same size and shape as the fixing part hole 51 formed in the resin part 50. However, such a hole is preferred that the opening area thereof is smaller than the projected area of the pressing part of the electrode terminal (i.e., the stimulating electrode pressing part 22 or the contact electrode pressing part 33) to the resin part 50.

A living body stimulating electrode apparatus 10 that is constituted by the living body stimulating electrode 1 thus produced as described above and a mounting part (including a cushioning member 70 and a protective sheet 80) will be described with reference to FIGS. 9A, 9B and 10.

Figure 9A:
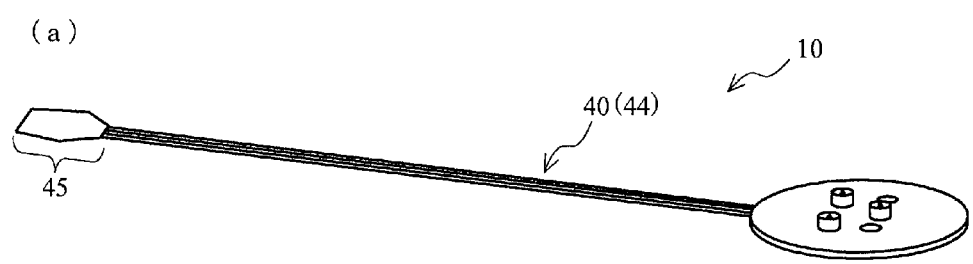
FIGS. 9A and 9B are perspective views showing an example of a living body stimulating electrode apparatus.
Figure 9B:
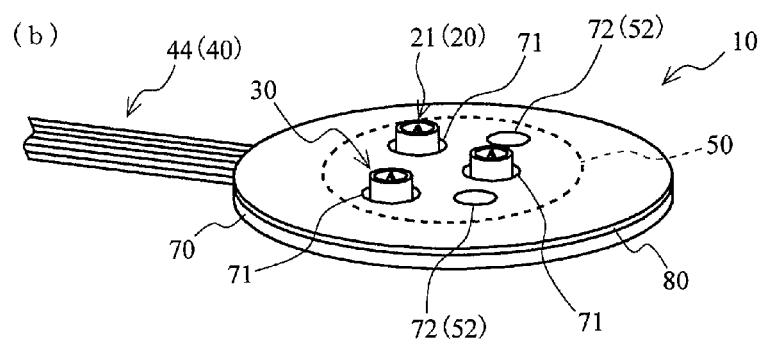
Figure 10:
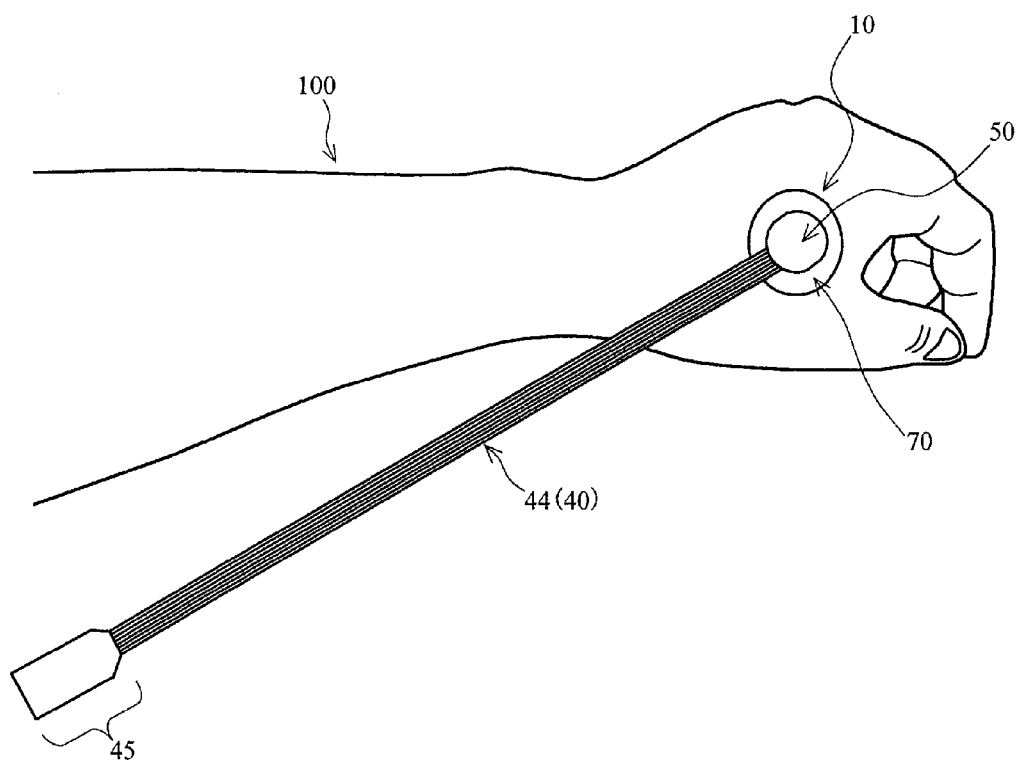
FIG. 10 is a perspective view showing an example of a living body stimulating electrode apparatus.

FIG. 9A is a schematic overall view showing the living body stimulating electrode apparatus 10, and FIG. 9B is an enlarged view showing a part of the apparatus that is in contact with a living body (e.g., a human body 100 shown in FIG. 10).

FIG. 10 is a perspective view showing an example of actual use of the living body stimulating electrode apparatus 10. In an actual state, the living body stimulating electrode apparatus 10 is connected to a controlling apparatus, which is not shown in the figures, via a connector 45 connected to a lead 44 of the flexible circuit board 40.

As shown in FIG. 9B, the living body stimulating electrode apparatus 10 has a living body stimulating electrode 1 and a mounting part for mounting the living body stimulating electrode 1 to a human body 100. The mounting part has a cushioning member 70 formed of medical sponge or the like having a fixing part hole K 71 and a positioning hole K 72, a protective sheet 80 formed of a film, and the like.

While not shown in the figures, a sticking material (such as a double-sided adhesive tape) capable of sticking the living body stimulating electrode 10 to the human body 100 after removing the protective sheet 80 is applied between the upper surface of the cushioning member 70 and the protective sheet 80. The surface of the living body stimulating electrode apparatus 10 (i.e., the surface thereof having the electrode protruding therefrom) may be stuck and fixed to the human body 100 as shown in FIG. 10.

A sticking material capable of sticking the cushioning member 70 to the flexible circuit board 40 after removing another protective sheet 80 is applied between the lower surface of the cushioning member 70 and the another protective sheet 80. The flexible circuit board 40 has a stick fixing hole 42 (see, FIGS. 1 and 2), and therefore the resin part 50 of the living body stimulating electrode 1 and the cushioning member 70 can fix the flexible circuit board 40 with the sticking material through the stick fixing hole 42 by pressing onto the lower surface of the cushioning material 70 even though the flexible circuit board 40 intervenes between the resin part 50 and the cushioning material 70.

Furthermore, the diameter of the resin part 50 is larger than the diameter of the flexible circuit board 40. Accordingly, the resin part 50 of the living body stimulating electrode 1 at the position outside the flexible circuit board 40 and the cushioning member 70 are stuck to each other by pressing onto the lower surface of the cushioning member 70, and thereby can fix the flexible circuit board 40.

According to the structure, the living body stimulating electrode 1 and the mounting part are stuck and fixed to each other in the positional relationship shown by the broken line in FIG. 9B.

In the living body stimulating electrode apparatus 10 having the structure shown above, by pressing the surface of the living body stimulating electrode 1 onto the skin of the human body 100, the contact part 31 of the contact electrode 30 is in contact with the skin, and the stimulating part 21 of the stimulating electrode 20 is stuck into the skin and reaches the pain sensory nerve.

On applying a voltage to the stimulating part 21 and the contact part 31, the pain sense is favorably stimulated by the stimulating part 21.

FIG. 11 is a table showing experimental results of the living body stimulating electrode apparatus 10 according to the first embodiment.

The item "Board material" is the material used as the resin part 50.

The item "Shape of terminal connecting portion" is the shape of the portion where the stimulating electrode pressing part 22 and the stimulating electrode fixing part 23 are connected to each other, in which R means a round shape (i.e., a curved line and a curved plane), and C means a chamfered shape.

The item "Dimension" is the dimension of the overlap for electric connection of the terminal connecting portion (unit: mm).

The item "Terminal withdrawing strength" is the holding strength described above (unit: kgf).

The item "Dispersion of implantation height" is a degree of the dispersion of the electrode terminal on pressing the living body stimulating electrode apparatus 10 onto the skin, and is specifically the distance between the overlap for electric connection A (see FIGS. 3B and 4B) and the flexible circuit board 40, and the electrode (stimulating electrode 20) in terms of dispersion from the standard value (unit: mm).

The item "Rate of occurrence of conduction failure" is the rate of occurrence of failure in supplying electric power (unit: %).

As shown in FIG. 11, the example G, in which the terminal connecting portion has a flat shape, undergoes a rate of occurrence of conduction failure that is suppressed to 10%, whereas the other examples, in which the terminal connecting portion has a round shape or a chamfered shape, undergo a rate of occurrence of conduction failure of 0%. It is understood from the results that the electric connection is strengthened to enhance the electric stability by using the terminal connecting portion having a round shape or a chamfered (i.e., the modified examples 1 to 4 above).

The examples A, B, C, D, E and F using PPS (polyphenylene sulfide resin) as the board material exhibit a terminal withdrawing strength of 1.0 kgf, whereas the example H using PP (polypropylene resin) as the board material exhibits a terminal withdrawing strength of 0.4 kgf, and the example I using PC (polycarbonate resin) as the board material exhibits a terminal withdrawing strength of 0.5 kgf, from which it is understood that in the case where materials that have a relatively low mechanical strength (i.e., PP and PC) are used, the terminal withdrawing strength of the electrode terminal is small, and the implantation height of the electrode terminal exhibits dispersion (which is 0.02 mm in both the examples H and I).

The first embodiment describes an example, in which both the electrode terminals (electrode pair) of the stimulating electrode 20 and the contact electrode 30 have the engaging part (i.e., the stimulating electrode pressing part 22 or the contact electrode pressing part 33), but the invention is not limited thereto.

As described in second and third embodiments below, such a structure may be used that any one electrode terminal of the electrode terminals (i.e., the stimulating electrode 20 and the contact electrode 30) constituting the electrode pair has a pressing part that functions as a part of the engaging part.

Second Embodiment

Figure 12A:
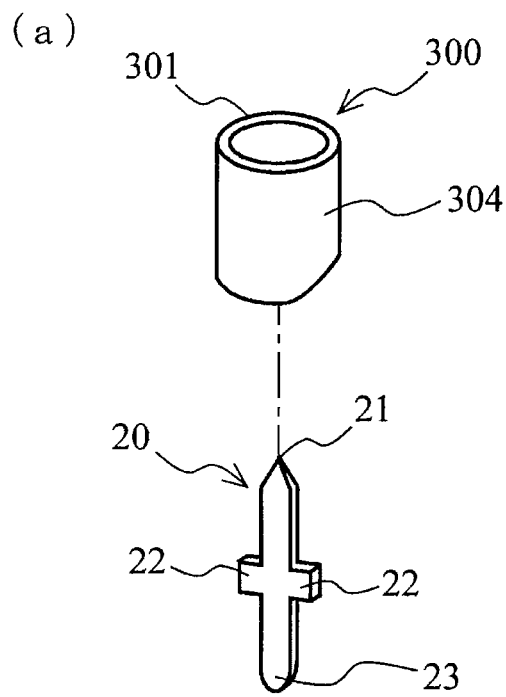
FIGS. 12A and 12B are perspective views showing examples of an electrode.

FIG. 12A is an enlarged view showing an electrode (i.e., a living body stimulating electrode 2) according to a second embodiment.

Figure 13:
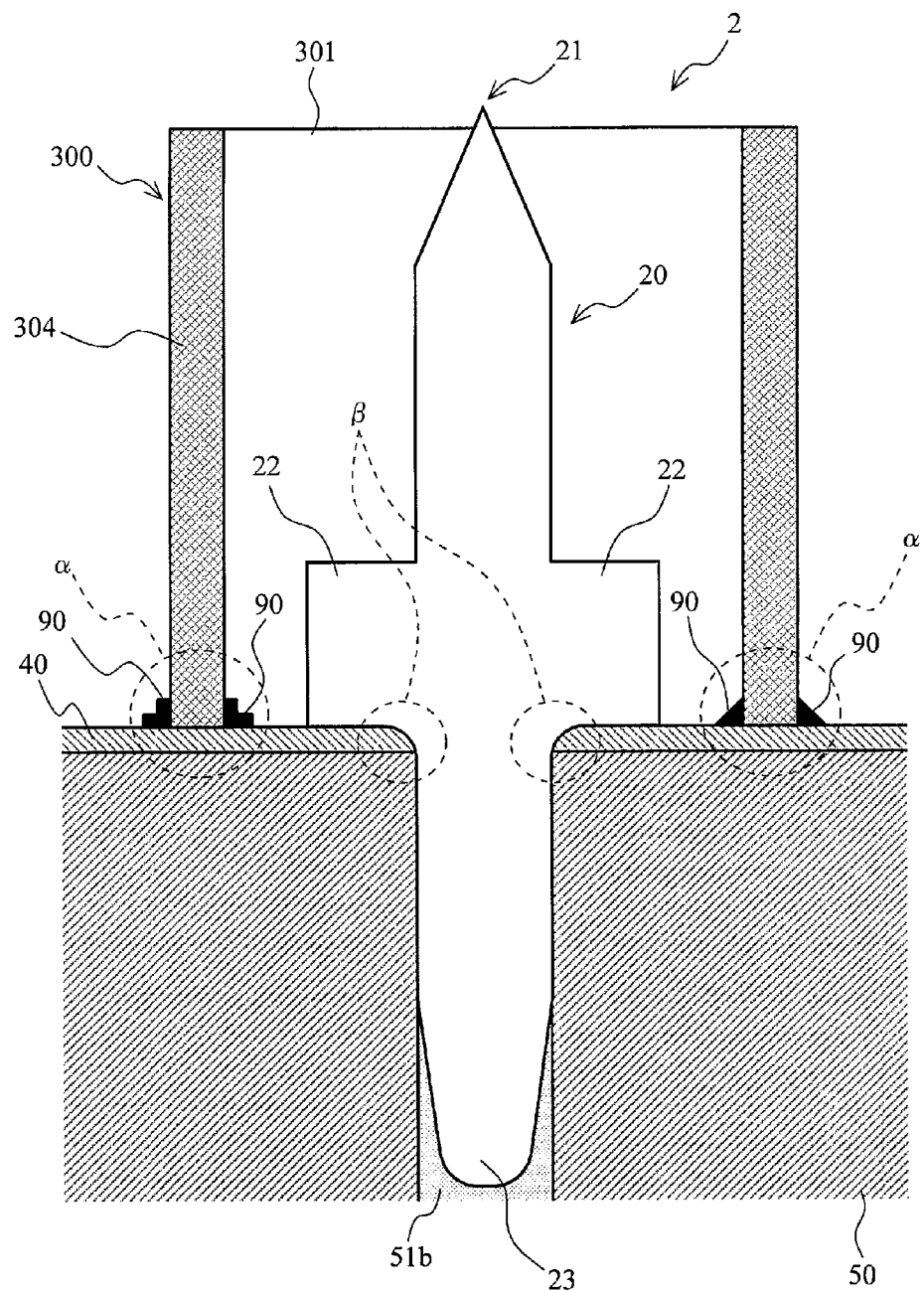
FIG. 13 is a schematic cross sectional view showing an example of an electrode.

FIG. 13 is an enlarged cross sectional view showing the living body stimulating electrode 2 according to the second embodiment.

The second embodiment is different from the first embodiment in such a point that a contact electrode 300 having no engaging part is used instead of the contact electrode 30 in the first embodiment.

In this case, a conductive adhesive 90 or the like may be used for fixing the contact electrode 300 and the flexible circuit board 40 to each other. Specifically, as shown by the symbol a in FIG. 13, the adhesive 90 is applied to the boundary between a cylindrical part 304 of the contact electrode 300 and the flexible circuit board 40, thereby connecting electrically the contact electrode 300 and the flexible circuit board 40.

Furthermore, as shown by the symbol β in FIG. 13, the stimulating electrode 20 and the flexible circuit board 40 are fixed to each other by pressing the flexible circuit board 40 with the stimulating electrode pressing part 22 and fixing and holding the stimulating electrode fixing part 23 by the resin part 50, and therefore the adhesive 90 may not be necessarily used.

Third Embodiment

Figure 12B:
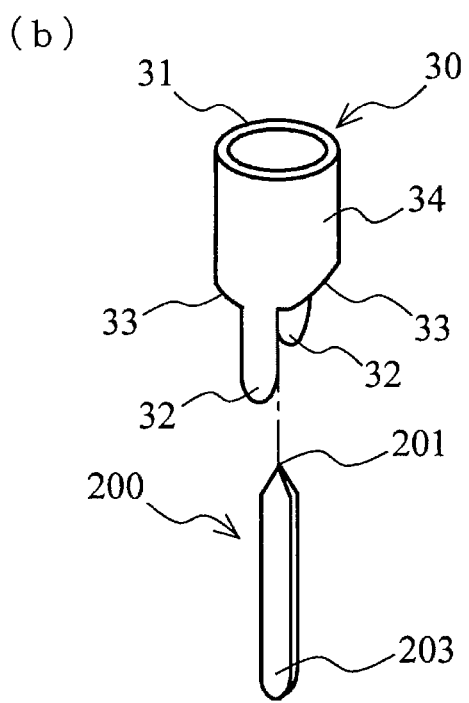

FIG. 12B is a view showing an electrode (i.e., a living body stimulating electrode 3) according to a third embodiment.

The living body stimulating electrode 3 is different from the first embodiment in such a point that a stimulating electrode 200 having no engaging part is used instead of the stimulating electrode 20 in the first embodiment. That is, the stimulating electrode 200 has no pressing part.

In this case, a conductive adhesive 90 or the like may be used for fixing the stimulating electrode 200 and the flexible circuit board 40 to each other. Specifically, an adhesive 90 is applied to the boundary between a stimulating electrode fixing part 203 of the stimulating electrode 200 and the flexible circuit board 40, thereby connecting electrically the stimulating electrode 200 and the flexible circuit board 40.

Furthermore, the contact electrode 30 and the flexible circuit board 40 are fixed to each other by pressing the flexible circuit board 40 with the contact electrode pressing part 33 and fixing and holding the contact electrode fixing part 32 by the resin part 50, and therefore the adhesive 90 may not be necessarily used.

In the third embodiment, the height positions of the stimulating electrode 200 and the contact electrode 30 (i.e., the protruding amount of the stimulating part 201 from the contact part 31) may be controlled by the depth of the fixing part hole J 51b formed in the resin part 50, or the like.

In the aforementioned embodiments, the fixing part hole F 41 (46) is formed in advance in the flexible circuit board 40, but the invention is not limited thereto. Specifically, such a structure may be used that no hole is formed in advance on the flexible circuit board 40, and the electrode terminal (i.e., the stimulating electrode 20 or the contact electrode 30) breaks through the flexible circuit board 40 at an appropriate position (i.e., a part capable of achieving electric connection).

In the aforementioned embodiments, one or both of the electrode terminals have a round plane or an inclined plane (i.e., a round shape or a chamfered shape) by the chamfering process at the contact surface to the flexible circuit board 40, and in addition to the structure, at least a part of the contact surface of the resin part 50 (i.e., the surface that is in contact with the electrode terminals with the flexible circuit board 40 intervening between them) may have the processed shape as similar to the aforementioned embodiments.

In this case, the dimension of the round shape provided on the resin part 50 (R for resin part) is preferably approximately half the dimension of the round shape provided on the engaging part of the electrode terminals (R for engaging part). Specifically, the dimension of the chamfering process (unit: mm) is preferably 0.1 for R for engaging part and 5/100 for R for resin part.

According to the structure, the efficiency of the process of inserting the electrode terminals to the resin part 50 may be enhanced.

The living body stimulating electrode that is used in the living body stimulating electrode apparatus 10 may be the living body stimulating electrode 2 according to the second embodiment or the living body stimulating electrode 3 according to the third embodiment instead of the living body stimulating electrode 1 according to the first embodiment.

Due to the structures, the living body stimulating electrodes according the aforementioned embodiments may provide the following advantageous effects.

(1) The use of the flexible circuit board reduces the weight of the electrode and simplifies the structure thereof.

(2) The use of the electrode for fixing (connecting) the flexible circuit board and the electrode to each other (i.e., the absence of an additional part, such as a connector on the board, for connecting the flexible circuit board and the electrode) avoids possible deterioration of the reliability of the connecting part (including the reliability in electric connection and the reliability in mechanical connection).

(3) The use of the electrode for fixing the flexible circuit board and the electrode to each other avoids the cost for the connector and soldering, the cost for the soldering process, and the like, and thus achieves reduction of the cost including the cost for parts and the cost for assembling process.

(4) The use of the electrode for fixing the flexible circuit board and the electrode to each other avoids increase of the weight due to the additional part, such as a connector, which is desirably reduced.

A method for producing the living body stimulating electrode apparatuses according to the aforementioned embodiments and modified embodiments (such as the living body stimulating electrode apparatus 10) will be described with reference to FIGS. 14 to 19.

Figure 14:
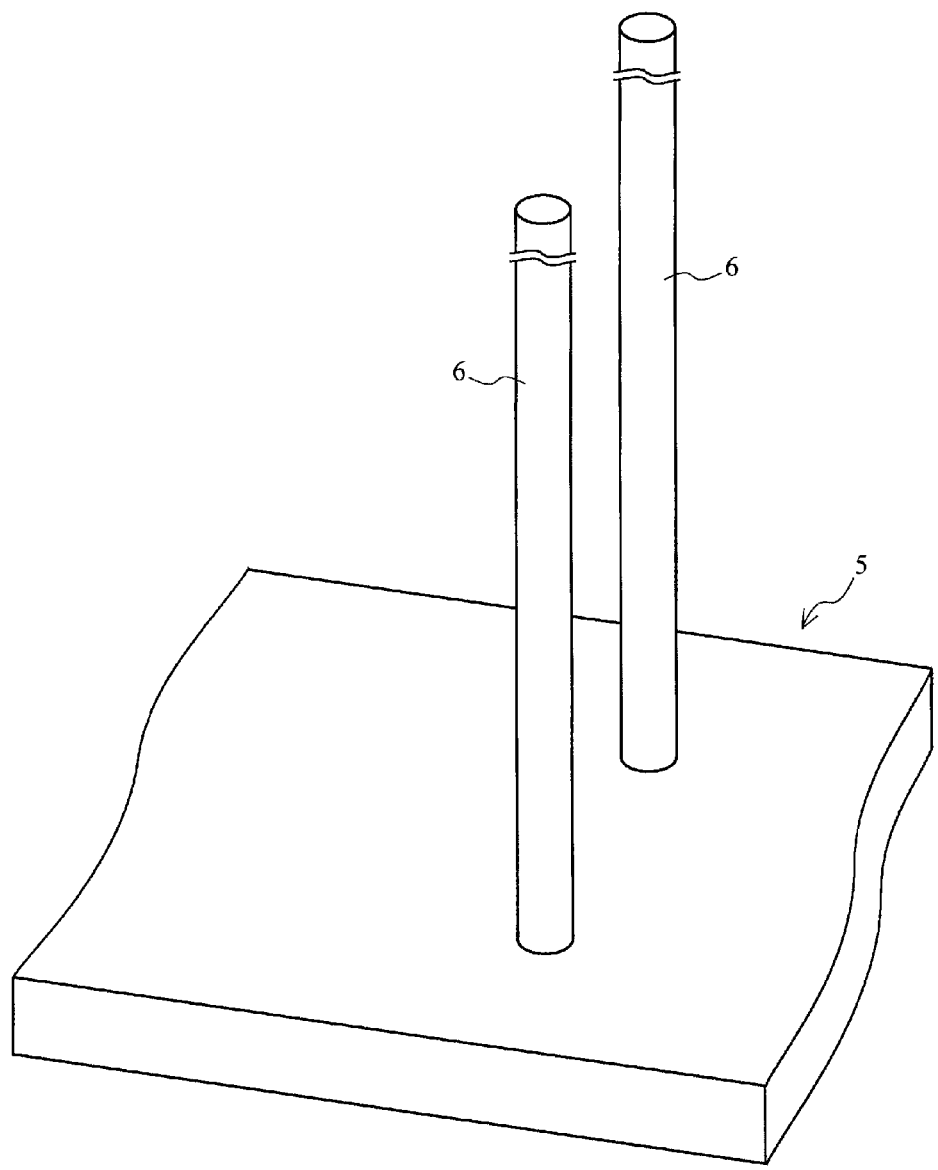
FIG. 14 is a perspective view showing an example of a method for producing a living body stimulating electrode.

In the production method for the embodiments and the modified embodiments, a working pedestal 5 having two positioning bars 6 as shown in FIG. 14 is preferably used as a positioning jig for the members. The positioning bar 6 functions as a guide column for disposing the members properly on the resin part 50 as a fixing base board, as described below.

The surface of the working pedestal 5 having the positioning bars 6 formed is referred to as an upper surface. In the member (part) that is disposed on the upper surface of the working pedestal 5 and positioned by the positioning bar 6, the surface thereof facing the upper surface of the working pedestal 5 is referred to as a lower surface, and the surface thereof opposite to the lower surface is referred to as an upper surface.

Figure 15:
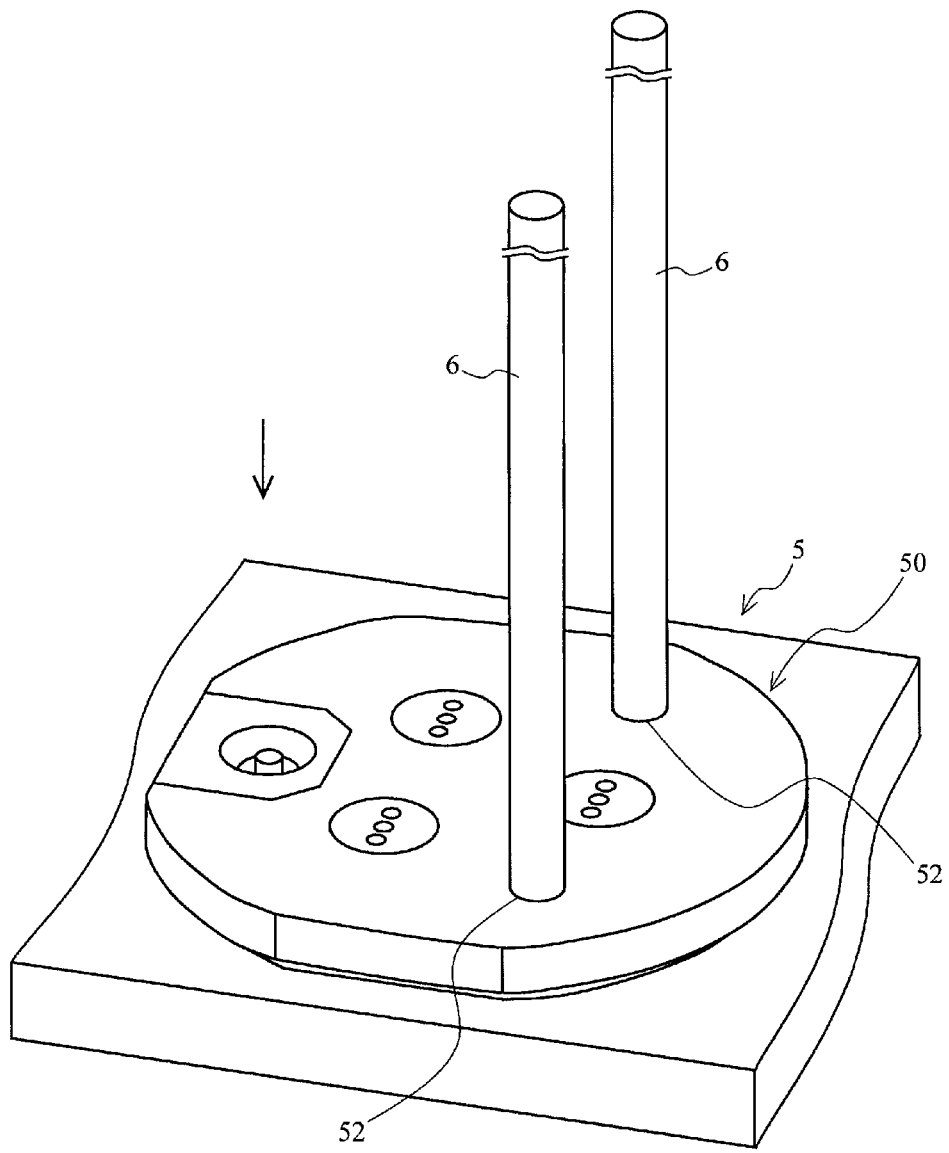
FIG. 15 is a perspective view showing an example of a method for producing a living body stimulating electrode.

In the first step, as shown in FIG. 15, the resin part 50 is disposed on the upper surface of the working pedestal 5. At this time, the resin part 50 is disposed in such a manner that the positioning bars 6 formed on the working pedestal 5 are penetrated through the positioning holes J 52 formed in the resin part 50. According to the procedure, the resin part 50 is positioned on the working pedestal 5.

Figure 16:
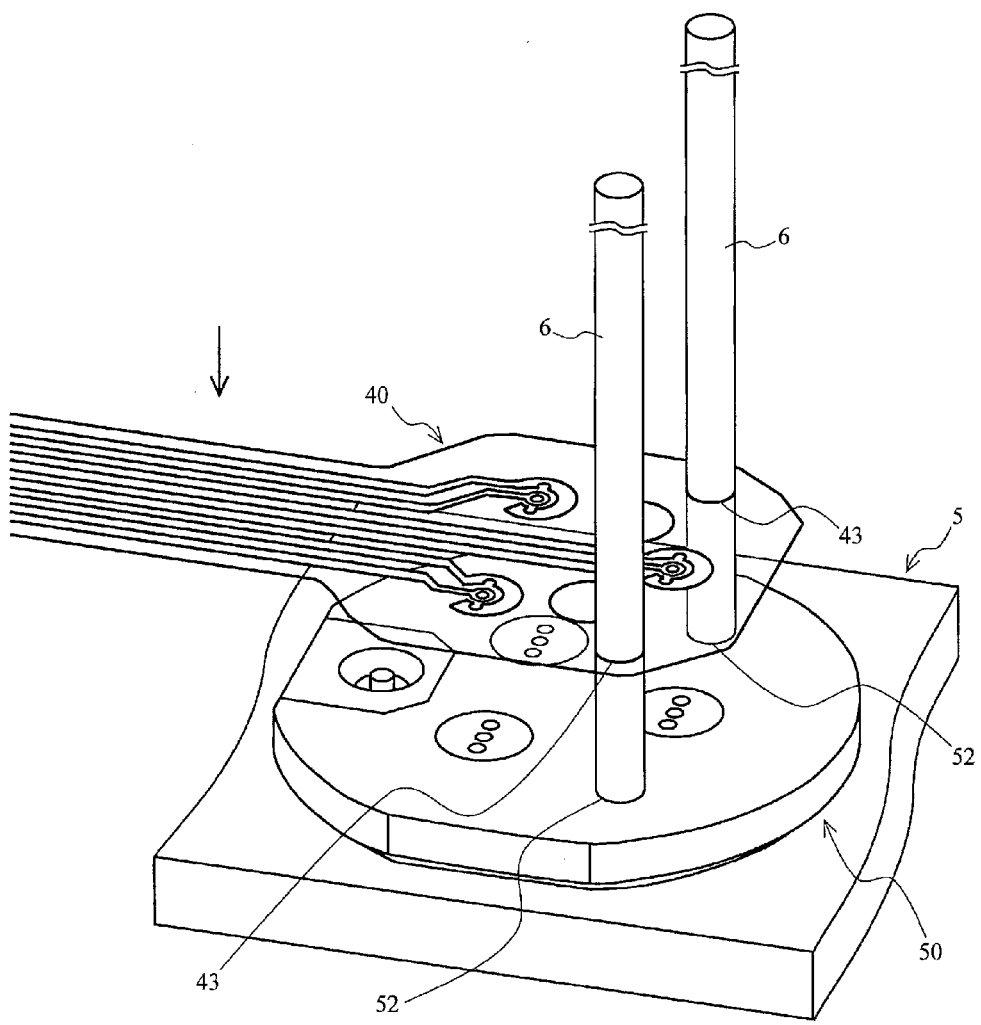
FIG. 16 is a perspective view showing an example of a method for producing a living body stimulating electrode.

In the next step, as shown in FIG. 16, the flexible circuit board 40 is disposed on the upper surface of the resin part 50 thus positioned. At this time, the flexible circuit board 40 is disposed in such a manner that the positioning bars 6, which have been penetrated through the positioning holes J 52 of the resin part 50, are penetrated through the positioning holes F 43 formed in the flexible circuit board 40. According to the procedure, the flexible circuit board 40 is positioned on the resin part 50 on the working pedestal 5.

Figure 17:
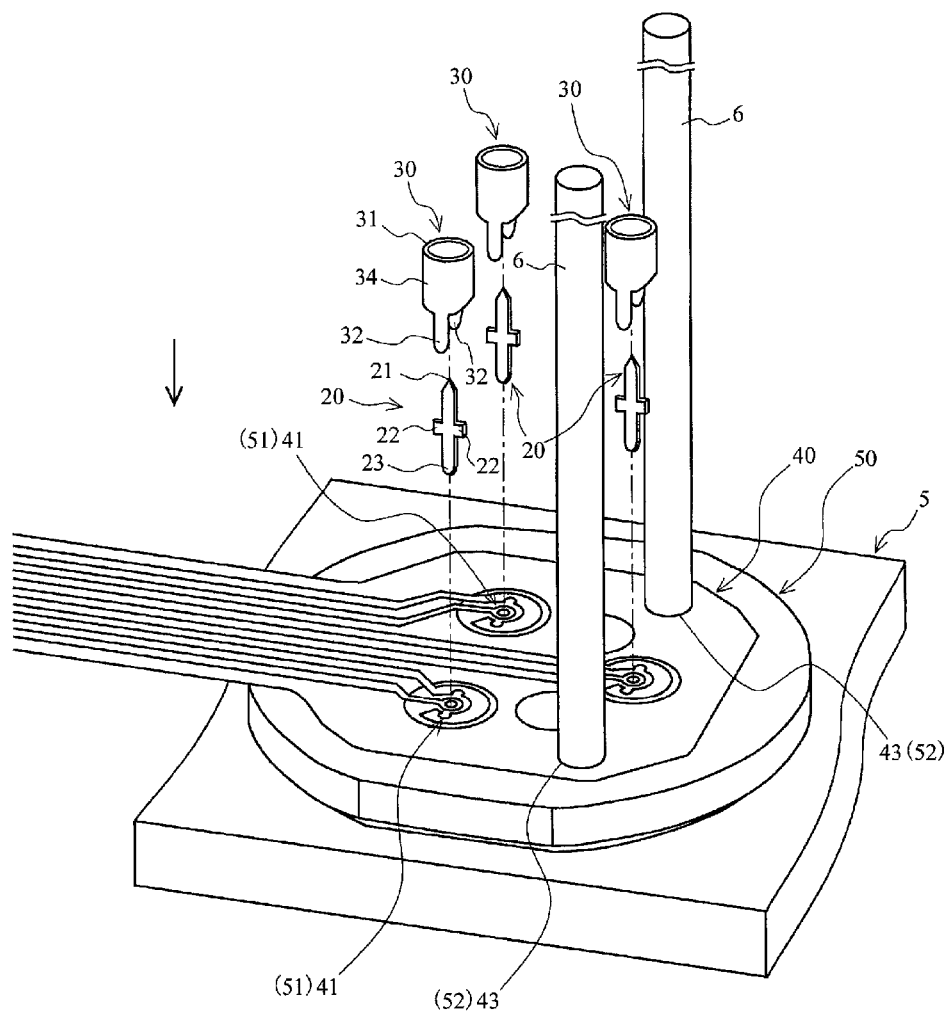
FIG. 17 is a perspective view showing an example of a method for producing a living body stimulating electrode.

In the next step, as shown in FIG. 17, the stimulating electrode 20 and the contact electrode 30 are disposed on the flexible circuit board 40 thus positioned, from the upper surface of the flexible circuit board 40.

According to the procedure, the fixing parts of the electrode terminals (i.e., the stimulating electrode fixing part 23 and the contact electrode fixing part 32) are passed through the fixing part holes F 41 of the flexible circuit board 40 and then engaged in (pressed into) the fixing part holes J 51 of the resin part 50, and thereby the stimulating electrode and the contact electrode 30 are fixed to and held by the resin part 50. This step (fixing and holding procedure) may be applied with any of the embodiments and modified embodiments described above.

Figure 18:
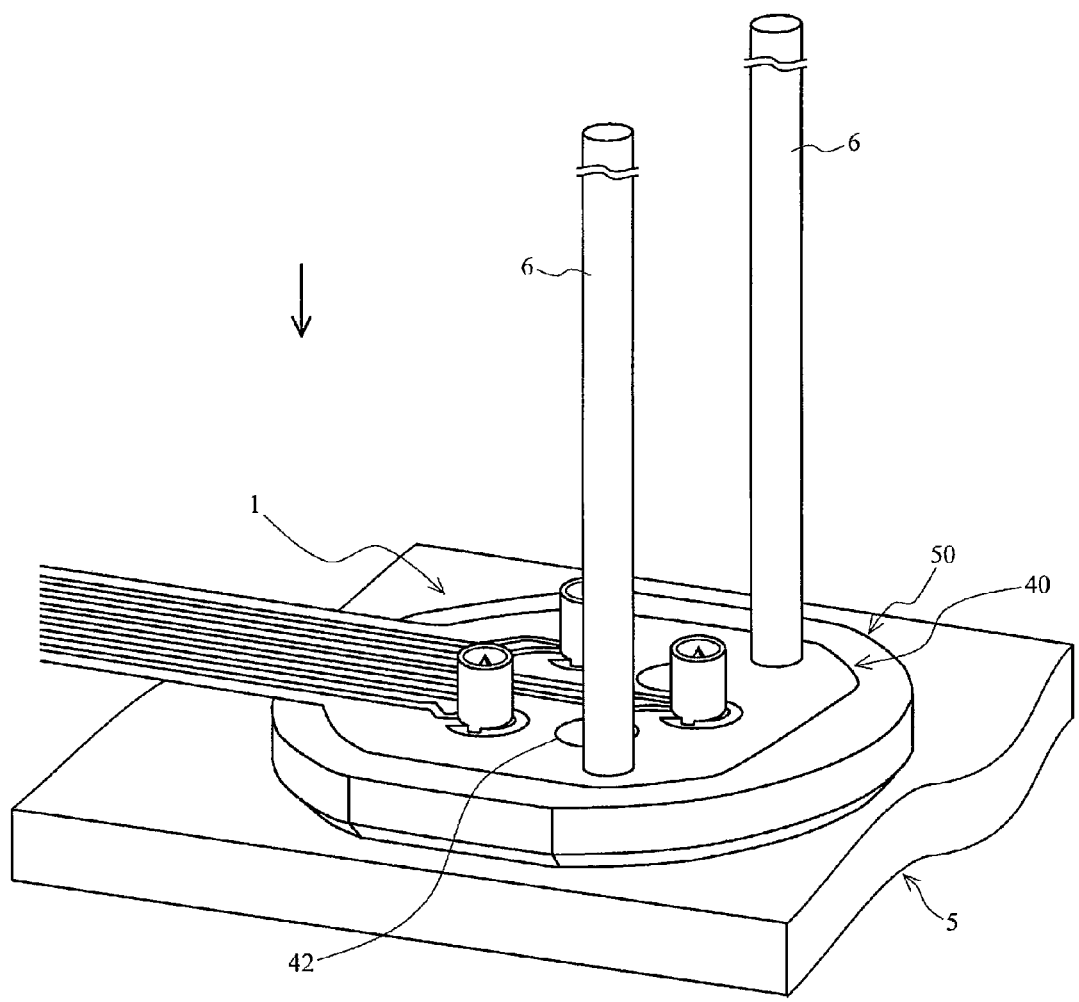
FIG. 18 is a perspective view showing an example of a method for producing a living body stimulating electrode.

According to the procedures up to this step, the living body stimulating electrode 1 having the members disposed at proper positions on the upper surface of the resin part 50 is completed as shown in FIG. 18.

Figure 19:
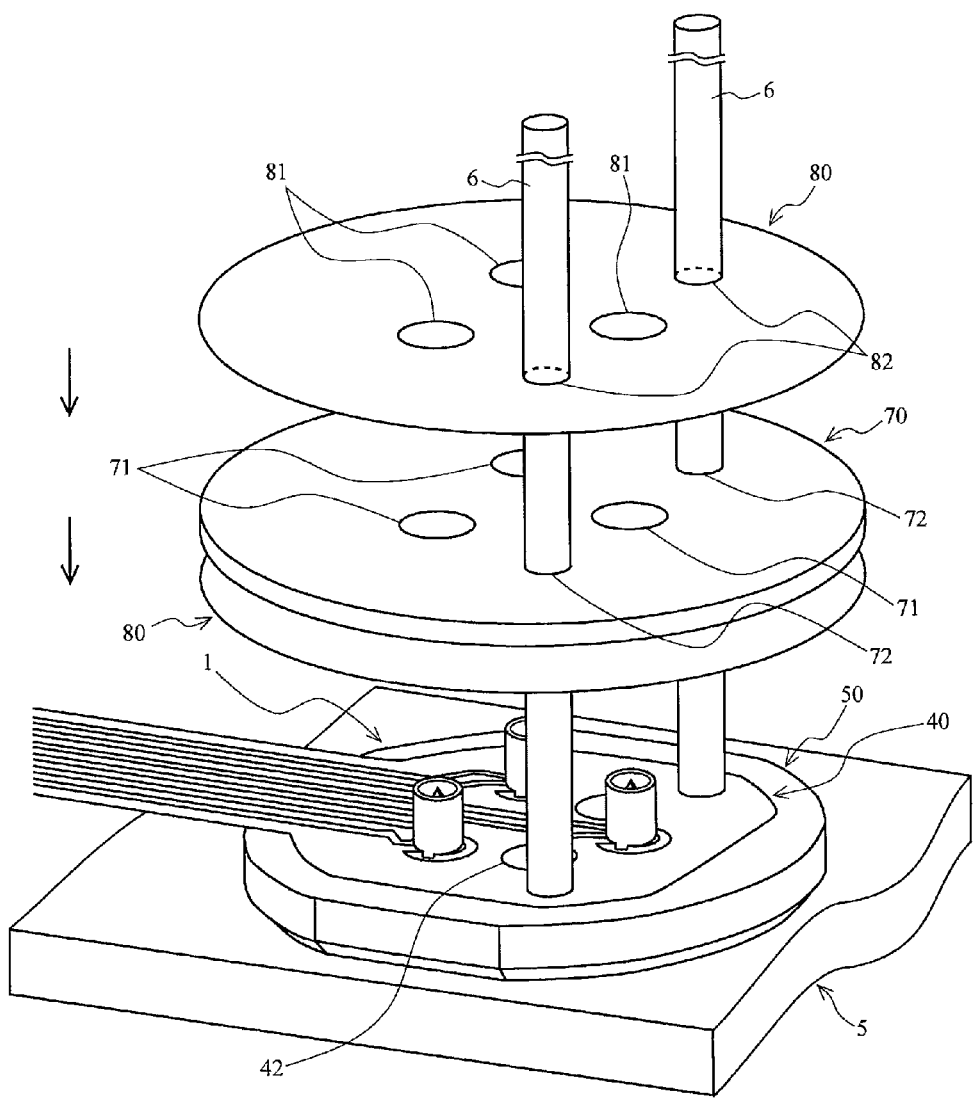
FIG. 19 is a perspective view showing an example of a method for producing a living body stimulating electrode.

In the next step, as shown in FIG. 19, the cushioning member 70, such as medical sponge, is disposed over the upper surface of the living body stimulating electrode 1 thus completed. Protective sheets 80 described later are disposed on the upper and lower surfaces of the cushioning member 70. For describing the procedure, FIG. 19 shows the state where the protective sheet 80 disposed on the lower surface of the cushioning member 70 is passed through the positioning bars 6 prior to the cushioning member 70.

At this time, the cushioning member 70 is disposed in such a manner that the positioning bars 6, which have been penetrated through the positioning holes F 43 of the flexible circuit board 40, are penetrated through the positioning holes K 72 formed in the cushioning member 70.

A sticking material is applied to the both surfaces (i.e., the upper and lower surfaces) of the cushioning member 70. The occupied area of the sticking material applied to the lower surface of the cushioning member 70 is preferably such an area that is larger than the outer circumference of the upper surface of the flexible circuit board 40 and is somewhat smaller than the resin part 50. As described for the first embodiment, the sticking material applied to the lower surface of the cushioning member 70 is stuck to the resin part 50 through the stick fixing hole 42 formed in the flexible circuit board 40, and thereby the cushioning member 70 and the resin part 50 are stuck and fixed to each other with the flexible circuit board 40 intervening between them.

Furthermore, the flexible circuit board 40 is fixed to the resin part 50 further firmly by the fixation through the outer circumference of the flexible circuit board 40 and the stick fixing hole 42, in addition to the fixation by pressing with the engaging parts (i.e., the stimulating electrode pressing part 22, the stimulating electrode fixing part 23, the contact electrode fixing part 32 and the contact electrode pressing part 33). In this case, the flexible circuit board 40 is fixed through the stick fixing hole 42, and thereby the flexible circuit board 40 is effectively prevented from being floated at the center part thereof.

In the final step, the protective sheet 80 is disposed over the upper surface of the cushioning member 70. At this time, the protective sheet 80 is disposed in such a manner that the positioning bars 6, which have been penetrated through the positioning holes K 72 of the cushioning member 70, are penetrated through the positioning holes H 82 formed in the protective sheet 80. The protective sheet 80 has a living body stimulating electrode hole 81, through which the living body stimulating electrode 1 is to protrude, and the living body stimulating electrode 1 protrudes from the living body stimulating electrode hole 81.

On sticking and fixing the living body stimulating electrode apparatus 10 thus completed to the human body 100 (see FIG. 10), the protective sheet 80 is removed, and the surface, from which the protective sheet 80 has been removed, is pressed onto the human body 100.

What is claimed is:
1. A living body stimulating electrode comprising:
a first electrode having a stimulating part at a tip of a first end thereof and having an acute angled shape configured to stimulate a skin of a living body,
a second electrode that has a contact part at a tip of a first end thereof that is configured to contact the skin of the living body through a line or a plane and has a fixed positional relationship with respect to the stimulating part of the first electrode, an engaging part in at least one of a second end of the first electrode and the second electrode, the engaging part having a fixing part that extends from the first end in a direction toward the second end, and a pressing part that extends in a lateral direction, an insulating board that fixes and holds the fixing part, and a flexible circuit board between the first electrode and the second electrode, and the insulating board, and having a circuit electrically connected to each of the first electrode and the second electrode, the engaging part being fixed to and held by the insulating board by the fixing part inserted into the insulating board and penetrating through the flexible circuit board, and thereby the pressing part is in contact with the circuit and presses and fixes the flexible circuit board to the insulating board.

2. The living body stimulating electrode according to claim 1, wherein the fixing part and the pressing part are continuous with at least a part thereof through an inclined plane or a curved plane, and a portion of the inclined plane or the curved plane on the side of the fixing part is fixed to and held by the insulating board, whereas another portion of the inclined plane or the curved plane on the side of the pressing part is in contact with the circuit, and presses and fixes the flexible circuit board to the insulating board.

3. The living body stimulating electrode according to claim 1, wherein the flexible circuit board has a first hole having a diameter such that the fixing part of the engaging part is in the first hole, and the pressing part thereof resides outside of the first hole, and in each of the first electrode, the second electrode, and the flexible circuit board, the fixing part penetrates through the first hole and is embedded in the insulating board and fixed thereto and held thereby.

4. The living body stimulating electrode according to claim 1, wherein the fixing part has a polygonal cross sectional shape, and the insulating board has a depressed part or a hole fixing and holding the fixing part and having an opening having a circular shape.

5. The living body stimulating electrode according to claim 4, wherein the depressed part or the hole in the insulating board and the fixing part are fixed to each other by an interference fit.

6. The living body stimulating electrode according to claim 1, wherein the insulating board includes a polyphenylene sulfide resin.

7. The living body stimulating electrode according to claim 1, wherein the living body stimulating electrode further comprises plural electrode pairs, each including a combination of the first electrode and the second electrode.

8. A living body stimulating electrode apparatus comprising:

the living body stimulating electrode according to claim 1, and a cushioning member fixed to the insulating board by sticking to a surface thereof and having the first electrode and the second electrode fixed thereto and held thereby, and includes through holes from which the first electrode and the second electrode protrude.

9. The living body stimulating electrode apparatus according to claim 8, wherein the flexible circuit board further includes a second hole in at least a part, and the cushioning member and the insulating board are fixed to each other by sticking through the second hole.

10. A method for producing a living body stimulating electrode comprising:

a first electrode having a stimulating part at a tip of a first end thereof having an acute angled shape configured to stimulate a skin of a living body, and an engaging part having a fixing part that extends from the first end toward a direction toward a second end and a pressing part that extends in a lateral direction, a second electrode having a contact part at a tip of a first end thereof that configured to contact the skin of the living body through a line or a plane and having a fixed positional relationship with respect to the stimulating part of the first electrode, and an engaging part having a fixing part that extends from the first end toward a second end and a pressing part that extends in a lateral direction, a flexible circuit board having a circuit that is electrically connected to each of the first electrode and the second electrode, and an insulating board having a first hole for the fixing part corresponding to the first electrode and a second hole for the fixing part corresponding to the second electrode, the method comprising:

a first step of placing the flexible circuit board on the insulating board, a second step of pressing the fixing part of the first electrode into the corresponding first hole of the insulating board with penetration through the flexible circuit board, until the pressing part of the first electrode is in electrical contact with the circuit of the flexible circuit board, and at the contact part, the flexible circuit board is pressed and fixed to the insulating board, and a third step of pressing the fixing part of the second electrode into the corresponding second hole of the insulating board with penetration through the flexible circuit board, until the pressing part of the second electrode is in electrical contact with the circuit of the flexible circuit board, and at the contact part, the flexible circuit board is pressed and fixed to the insulating board.

* * * * *